(12) United States Patent
Adams et al.

(10) Patent No.: US 6,624,295 B1
(45) Date of Patent: Sep. 23, 2003

(54) HUMAN ANTI-FACTOR IX/IXA ANTIBODIES

(75) Inventors: Camellia W. Adams, Mountainview, CA (US); Brigitte Devaux, Redwood City, CA (US); Dan L. Eaton, San Rafael, CA (US); Philip E. Hass, Moss Beach, CA (US); J. Kevin Judice, Montara, CA (US); Daniel Kirchhofer, Los Altos, CA (US); Shelley Suggett, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/383,667

(22) Filed: Aug. 26, 1999

Related U.S. Application Data

(60) Provisional application No. 60/122,767, filed on Mar. 3, 1999, and provisional application No. 60/098,233, filed on Aug. 28, 1998.

(51) Int. Cl.⁷ ............................................. C07H 21/04

(52) U.S. Cl. ................................................. 536/23.53

(58) Field of Search ...................... 536/23.53; 435/69.6, 435/91.1, 320.1, 252.3

(56) References Cited

U.S. PATENT DOCUMENTS 5,654,407 A    8/1997   Boyle et al.

FOREIGN PATENT DOCUMENTS

| WO | WO 91/16353 | 10/1991 |
| WO | WO 95/25167 | 9/1995 |
| WO | WO 97/26010 | 7/1997 |

OTHER PUBLICATIONS

Lewis et al. Blood 56(4):608–614, 1980.*
Figini et al. J. Mol. Biol. 239:68–78, 1994.*
Janeway et al (1999) Immunobiology 4th Edition, Garland Press, London NY p. 87.*
Ahmad and Walsh, "Platelet membrane–mediated coagulation protease complex assembly" *Trends in Cardiovascular Medicine* 4(6):271–277 (1994).
Ahmad et al., "Coagulation factor IX residues $G_4$–$Q_{11}$ mediate its interaction with a shared factor IX/IXa binding site on activated platelets but not the assembly of the functional factor X activating complex" *Biochemistry* 37(6):1671–1679 (Feb. 10, 1998).
Ahmad et al., "High–affinity, specific factor IXa binding to platelets is mediated in part by residues 3–11" *Biochemistry* 33(40):12048–12055 (Oct. 11, 1994).
Bach, R. R., "Initiation of Coagulation by Tissue Factor" *CRC Critical Reviews in Biochemistry* 23(4):339–368 (1988).
Benedict et al., "Active site–blocked factor IXa prevents intravascular thrombus formation in the coronary vasculature without inhibiting extravascular coagulation in a canine thrombosis model" *Journal of Clinical Investigation* 88(5):1760–1765 (Nov. 1991).
Blackburn et al., "Anti–factor IX monoclonal antibody, BC2, is a potent antithrombotic agent" *Blood* (Abstract #1885) 90(Suppl. 1):424a–425a (1997).
Cheung et al., "Identification of the endothelial cell binding site for factor IX" *Proc. Natl. Acad. Sci. USA* 93(20):11068–11073 (Oct. 1, 1996).
Cheung et al., "The binding of human factor IX to endothelial cells is mediated by residues 3–11" *Journal of Biological Chemistry* 267(29):20529–20531 (Oct. 15, 1992).
Davie et al., "The Coagulation Cascade: Initiation, Maintenance, and Regulation" *Biochemistry* 30(43):10363–10370 (Oct. 29, 1991).
Di Scipio et al., "Activation of human factor IX (Christmas factor)" *Journal of Clinical Investigation* 61(6):1528–1538 (Jun. 1978).
Fujikawa et al., "The mechanism of activation of bovine factor IX (Christmas factor) by bovine factor $XI_a$ (activated plasma thromboplastin antecedent)" *Biochemistry* 13(22):4508–4516 (Oct. 22, 1974).
Heimark and Schwartz, "Binding of coagulation factors IX and X to the endothelial cell surface" *Biochemical & Biophysical Research Communications* 111(2):723–731 (Mar. 16, 1983).
Lewis et al., "Isolation of $CA^{++}$–dependent human antibodies to human factor IX" *Circulation* (abstract #1070) 62(4):III–279 (Oct. 1980).
Liebman et al., "The factor IX phospholipid–binding site is required for calcium–dependent activation of factor IX by factor XIa" *Journal of Biological Chemistry* 262(16):7605–7612 (Jun. 5, 1987).
Liebman, H., "The metal–dependent conformational changes in factor IX associated with phospholipid binding. Studies using antibodies against a synthetic peptide and chemical modification of factor IX" *European Journal of Biochemistry* 212(2):339–345 (Mar. 1, 1993).
Mann et al., "Surface–dependent hemostasis" *Seminars in Hematology* 29(3):213–226 (Jul. 1992).
Osterud and Rapaport, "Activation of factor IX by the reaction product of tissue factor and factor VII: additional pathway for initiating blood coagulation" *Proc. Natl. Acad. Sci. USA* 74(12):5260–5264 (Dec. 1977).

(List continued on next page.)

Primary Examiner—Patrick J. Nolan
Assistant Examiner—Amy DeCloux
(74) Attorney, Agent, or Firm—Craig G. Svoboda; Jeffery S. Rubinec

(57) ABSTRACT

The invention provides for the isolation, identification, synthesis, expression and purification of antibodies reactive with factor IX (FIX)/factor IXa (IXa). In particular aspects, the invention provides human antibodies reactive with the human FIX Gla domain. The invention further provides compositions especially pharmaceutical compositions, articles of manufacture, and methods of inhibiting the activation of-FIX and inhibiting FIX/IXa dependent coagulation.

8 Claims, 13 Drawing Sheets-

OTHER PUBLICATIONS

Osterud et al., "Human blood coagulation factor IX. Purification, properties, and mechanism of activation by activated factor XI" *Journal of Biological Chemistry* 253(17):5946–5951 (Sep. 10, 1978).

Pike et al., "Immunochemical characterization of a monoclonal γG4, λ human antibody to factor IX" *Blood* 40(1):1–10 (Jul. 1972).

Prorok et al., "The entire γ–carboxyglutamic acid– and helical stack–domains of human coagulation factor IX are required for optimal binding to its endothelial cell receptor" *International Journal of Peptide & Protein Research* 48:281–285 (1996).

Rawala–Sheikh et al., "Role of γ–carboxyglutamic acid residues in the binding of factor IXa to platelets and in factor–X activation" *Blood* 79(2):398–405 (Jan. 15, 1992).

Refino et al., "A human antibody that binds to the γ–carboxyglutamic acid domain of factor IX is a potent antithrombotic in vivo" *Thombosis and Haemostasis* 82(3):1188–1195 (Sep. 1999).

Reisner et al., "Immunochemical characterization of a polyclonal human antibody to factor IX" *Blood* 50(1):11–19 (Jul. 1977).

Ryan et al., "Structural determinants of the factor IX molecule mediating interaction with the endothelial cell binding site are distinct from those involved in phospholipid binding" *Journal of Biological Chemistry* 264(34):20283–20287 (Dec. 5, 1989).

Sekiya et al., "Regulation of the tertiary structure and function of coagulation factor IX by magnesium (II) ions" *Journal of Biological Chemistry* 270(24):14325–14331 (Jun. 16, 1995).

Spanier et al., "Heparinless cardiopulmonary bypass with active–site blocked factor IXa: a preliminary study on the dog" *Journal of Thoracic & Cardiovascular Surgery* 115(5):1179–1188 (May 1998).

Suggett et al., "Use of phage display for the generation of human antibodies that neutralized factor IX function" *Blood* (abstract #2266) 92(10 suppl. 1):551a (Nov. 15, 1998).

Sugo et al., "Anti–human factor IX monoclonal antibodies specific for calcium ion–induced conformations" *Thrombosis Research* 58(6):603–614 (Jun. 15, 1990).

Toomey et al., "The endothelial cell binding determinant of human factor IX resides in the γ–carboxyglutamic acid domain" *Biochemistry* 31(6):1806–1808 (Feb. 18, 1992).

Wong et al., "Relative efficacy of active site–blocked factors IXa, Xa in models of rabbit venous and arterio–venous thrombosis" *Thrombosis and Haemostasis* 77(6):1143–1147 (Jun. 1997).

Yoshitake et al., "Nucleotide sequence of the gene for human factor IX (antihemophilic factor B)" *Biochemistry* 24(14):3736–3750 (Jul. 2, 1985).

Zhong et al., "Some human inhibitor antibodies interfere with factor VIII binding to factor IX" *Blood* 92(1):136–142 (Jul. 1, 1998).

Stenflo and Dahlback, "Vitamin K–Dependent Proteins" *The Molecular Basis of Blood Diseases*, Stamatoyannopoulos et al. eds., 2nd edition, Philadelphia, PA:Saunders pps. 565–598 (1994).

Limentani et al. *Hemostasis and Thrombosis Basic Principles and Clinical Practice, Chapter 5*, Coleman et al. Eds., Third edition, Philadelphia:Lippincott Company (1994) pp. 94–108.

\* cited by examiner

SEQUENCE HOMOLOGY BETWEEN FACTOR IX Gla DOMAINS FROM VARIOUS SPECIES

|  | | 10 | | 20 | | 30 | | 40 | |
|---|---|---|---|---|---|---|---|---|---|
| human | Y N S G K L E E F V Q G N L E R E C M E E K C S F E E A R E V F E N T E R T T E F W K |
| canine | Y N S G K L E E F V R G N L E R E C I E E K C S F E E A R E V F E N T E K T T E F W K |
| murine | Y N S G K L E E F V R G N L E R E C I E E R C S F E E A R E V F E N T E K T T E F W K |
| rabbit | Y N S G K L E E F V S G N L E R E C I E E R C S F E E A R E V F E N T E K T T E F W K |

FIG._1A

SEQUENCE HOMOLOGY BETWEEN Gla DOMAINS OF VARIOUS HUMAN COAGULATION PROTEINS

|  | | 10 | | 20 | | 30 | | 40 | |
|---|---|---|---|---|---|---|---|---|---|
| factor IX | Y N S G K L E E F V Q G N L E R E C M E E K C S F E E A R E V F E N T E R T T E F W K |
| factor X | A - - - M K K H - - - - - - - - - T - Y - - - - - - - - - - D S D K N - - I |
| factor VII | A - - - L R P S - - - - - - - - - K Q - - - - I K D A - - - - - K L - - - I |
| Protein C | A - - - L R H S S - - - - - - - - I D - - - - K I Q V D D - - - - - L A - - S |
| Prothromb. | A - - - V R K - - - - - - - - - - V T Y - - - F - A L - - - - - S S T A D V A |

FIG._1B

| CLONE # | HEAVY CHAINS | | | | LIGHT CHAINS | | | |
|---|---|---|---|---|---|---|---|---|
| | Family | CDR1 | CDR2 | CDR3 | Family | CDR1 | CDR2 | CDR3 |
| 10C12 | VH3 | TYAMH | IISYDGSKKYYADSVKG | ASIAAARVLDY | Vλ1 | SGSTSNIGNNYVS | DVSKRPS | AAWDDSLS-EFL |
| 11C5 | VH3 | TYAMH | VISYDGSNKYYADSVKG | SDYGGN-LGEF | Vλ1 | SGSTSNIGNNYVS | DVSKRPS | AAWDDSLS-EFL |
| 11G9 | VH3 | TYAMH | IISYDGSNKYYADSVKG | ASIAAGRVLDY | Vλ1 | SGSTSNIGNNYVS | DVSKRPS | AAWDDSLS-EFL |
| 13D1 | VH3 | TYAMH | IISYDGSKKYYADSVKS | ASIAAARVLDY | Vλ1 | SGSTSNIGNNYVS | DVSKRPS | AAWDDSLS-EFL |
| 13H6 | VH3 | SYAMH | VISHDGGKKEYADSVRG | AAYTAATIADN | Vλ1 | TGSSR---DVDVS | EVSKRPS | SSYGGSN--NVV |
| 14H9 | VH3 | DYAMH | TISPSGRSTYNADSVKG | RGIGYKGGFDV | Vλ1 | SGGRSNIGSNTVK | GNDQRPS | QSYDSSLRGSRV |

| CLONE # | CONCENTRATION (uM) | AFFINITY |
|---|---|---|
| 10C12 | 0.8 | 1.6 nM |
| 13D1 | 0.73 | 2.9 nM |
| 13H6 | 1.1 | 0.46 nM |
| 14H9 | 1.9 | ND |

FIG._3

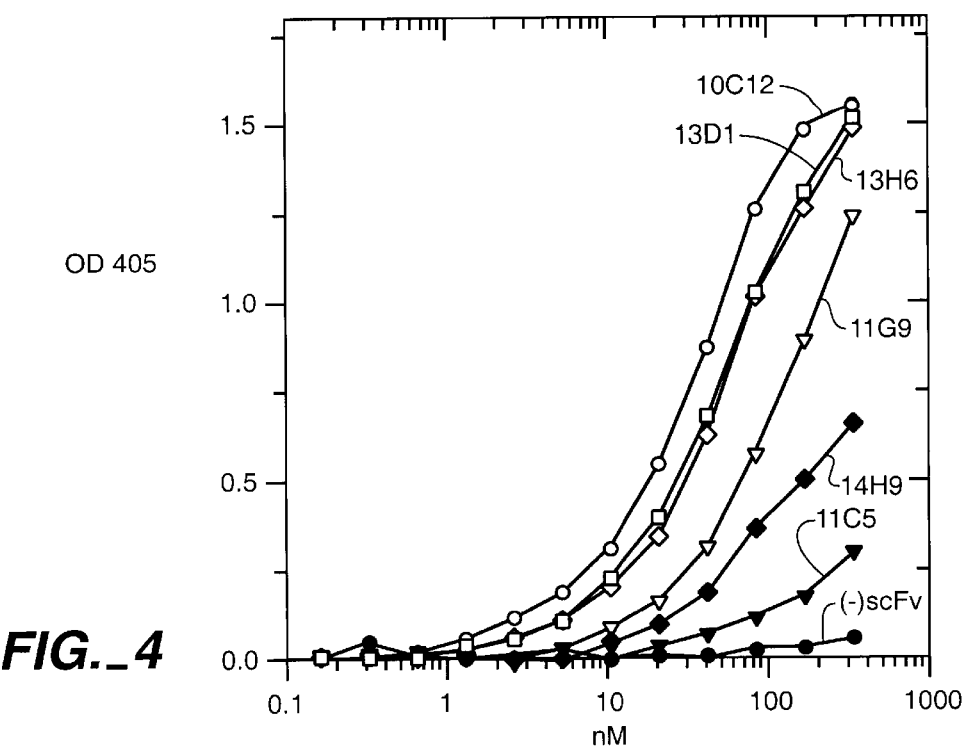
FIG._4
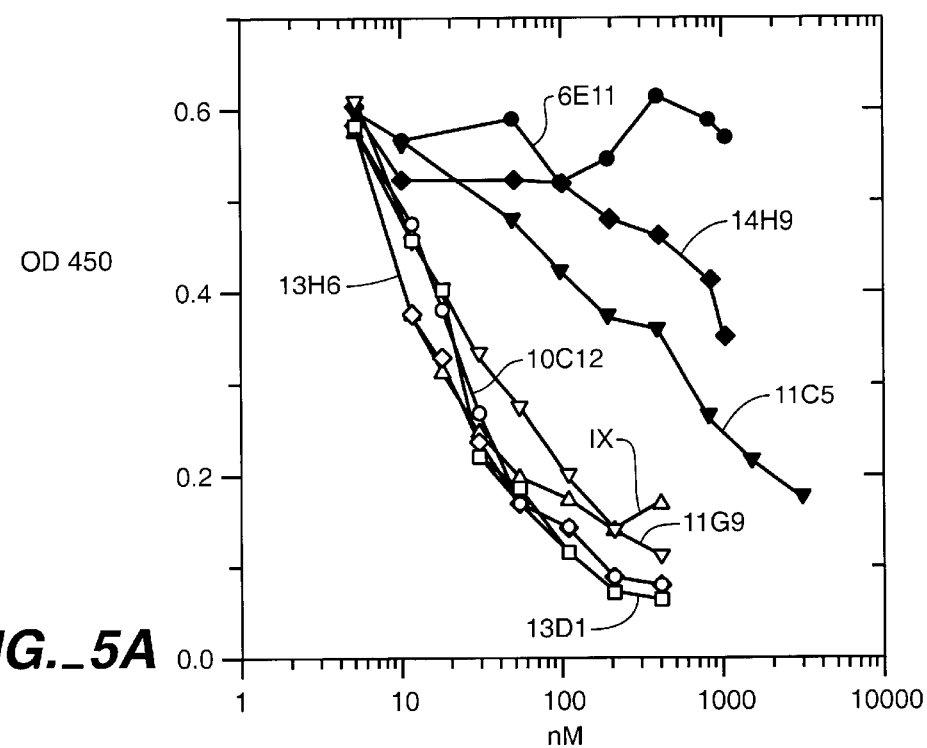
FIG._5A

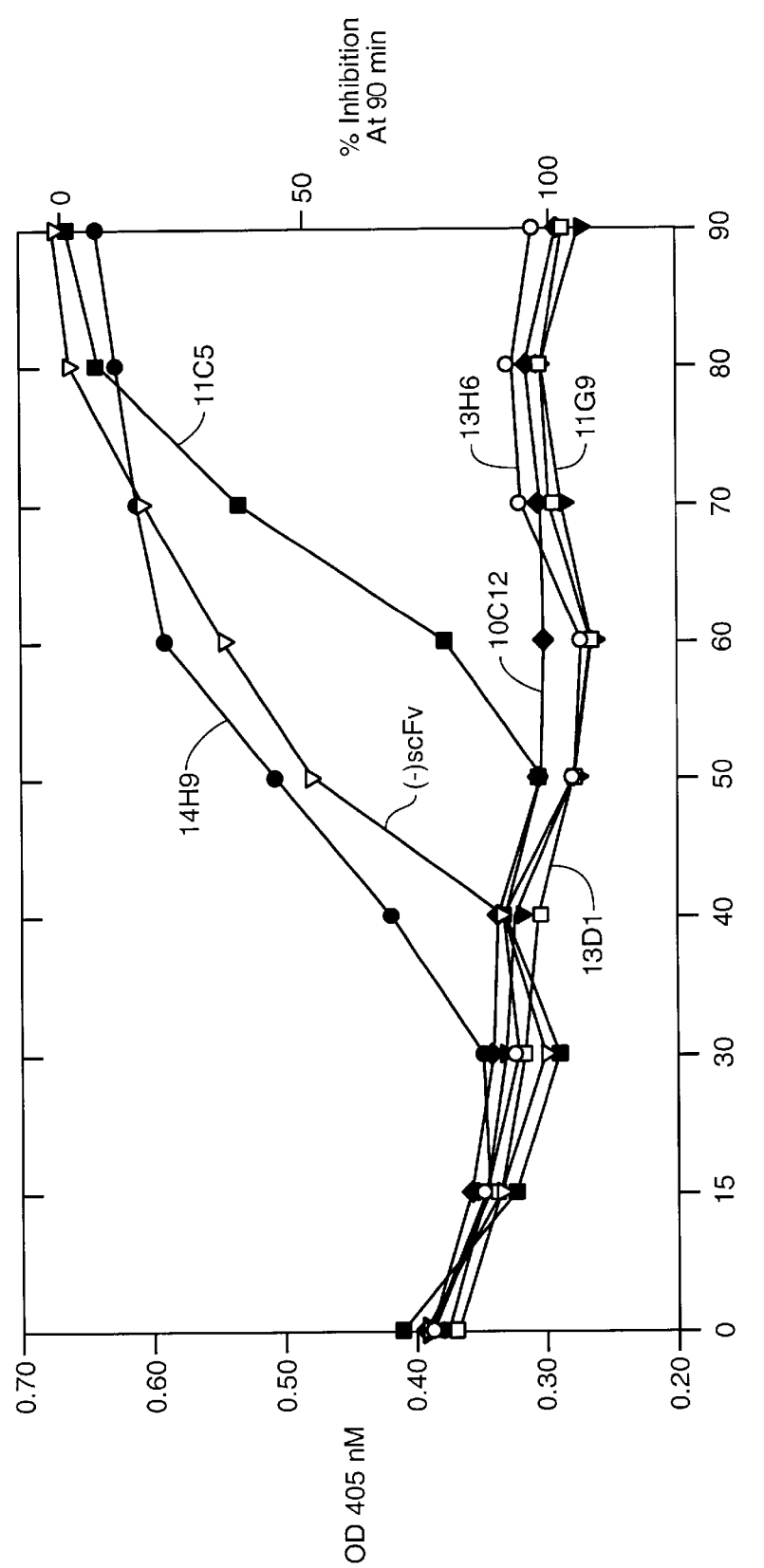
FIG._5B

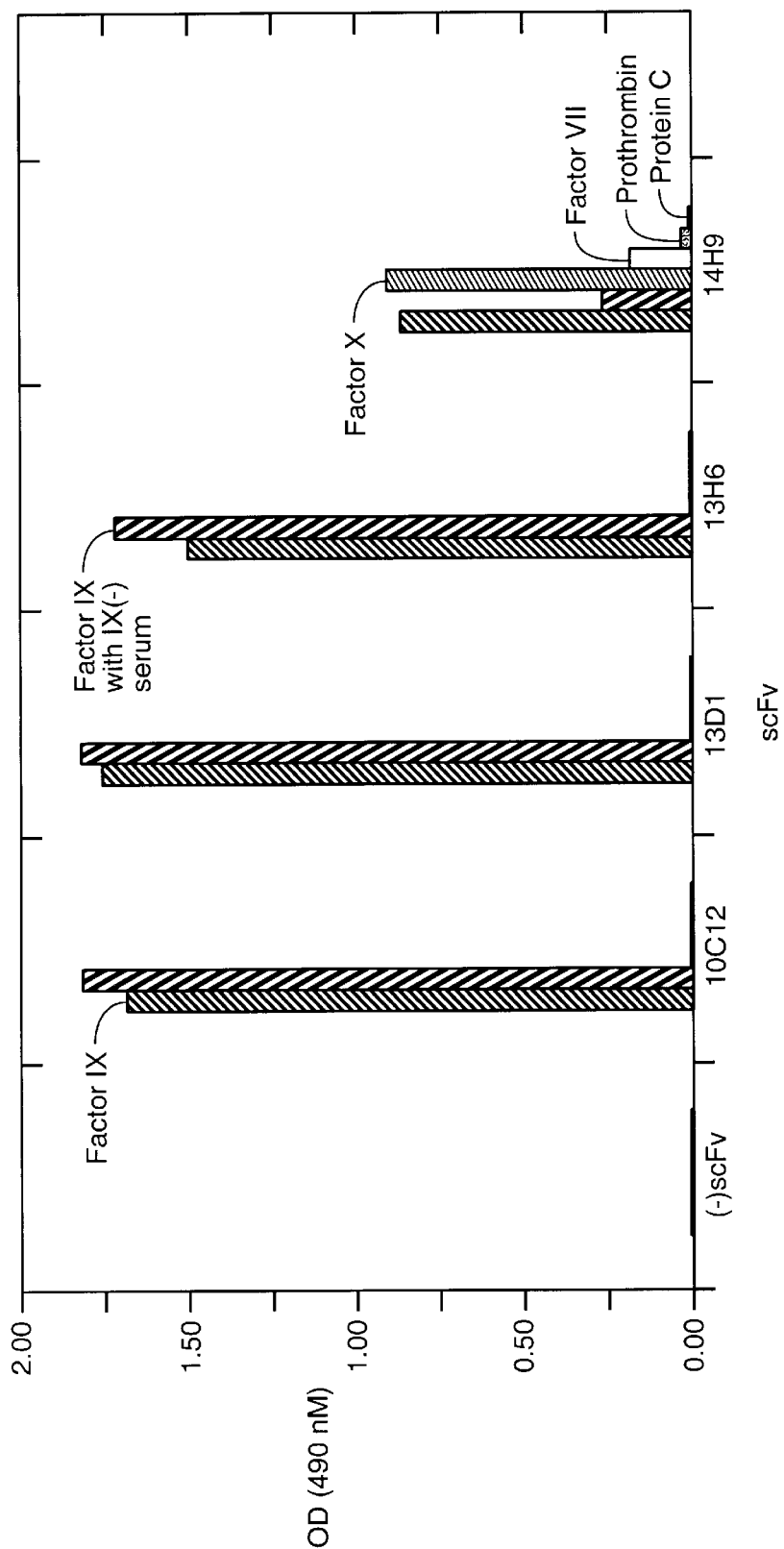
FIG._6A

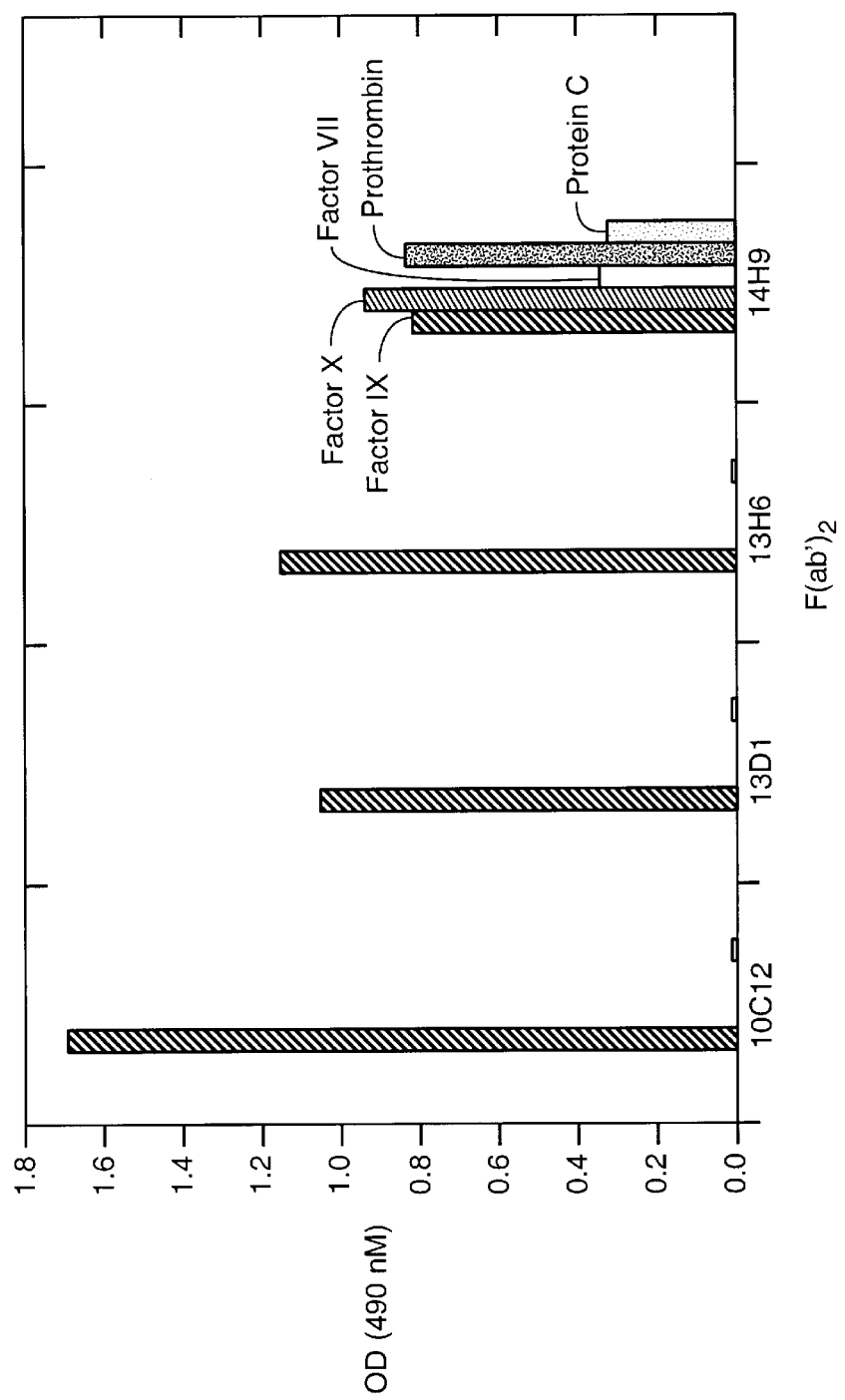
FIG._6B

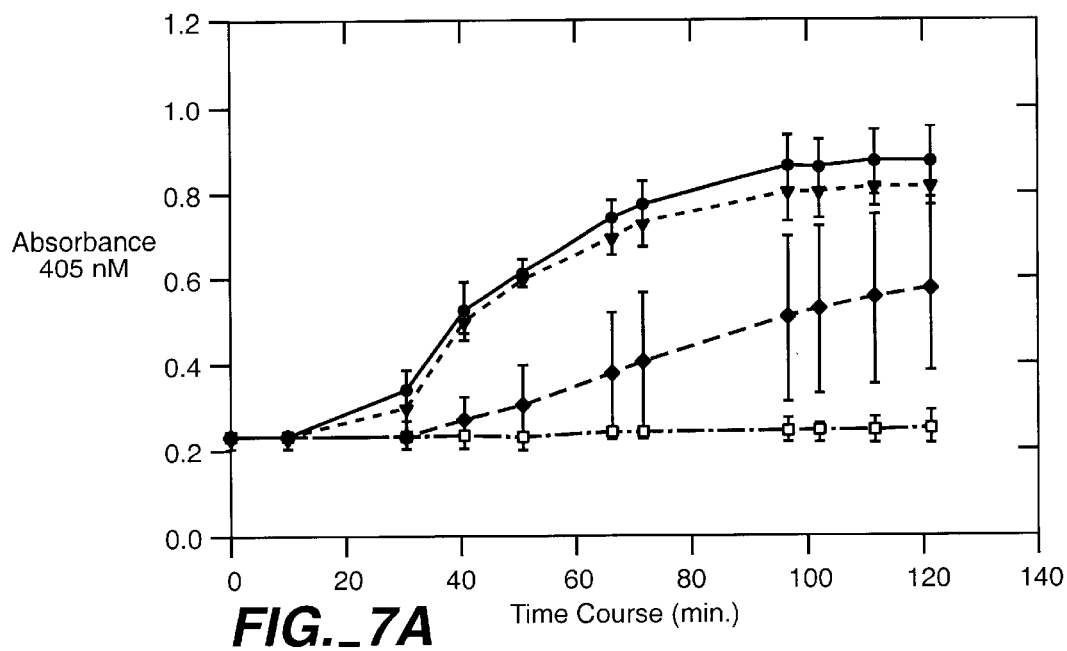
FIG._7A
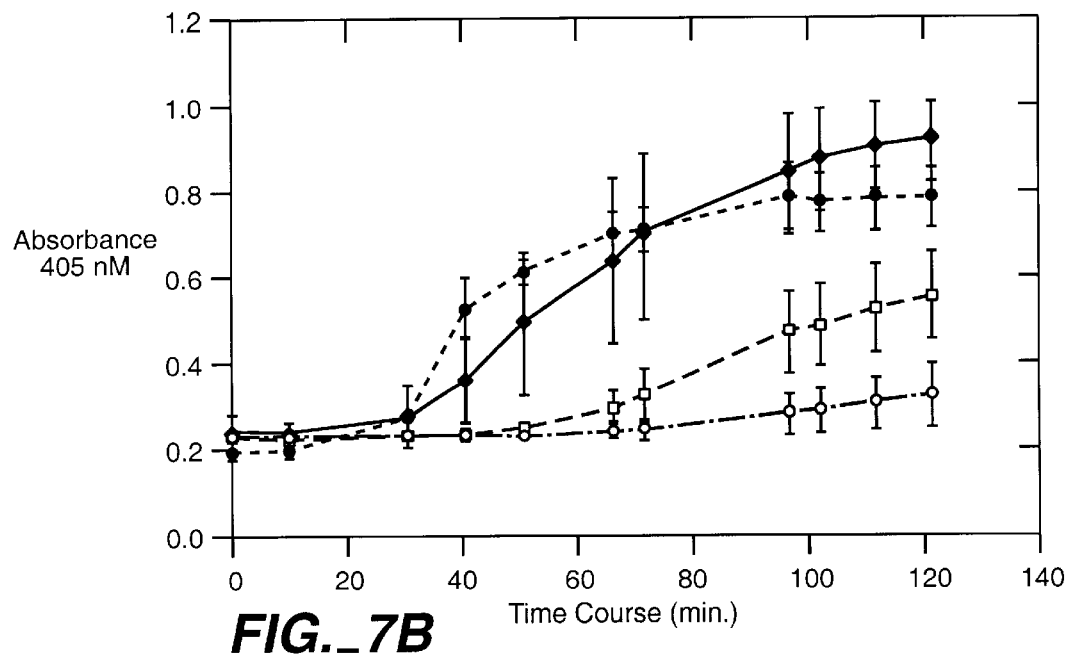
FIG._7B

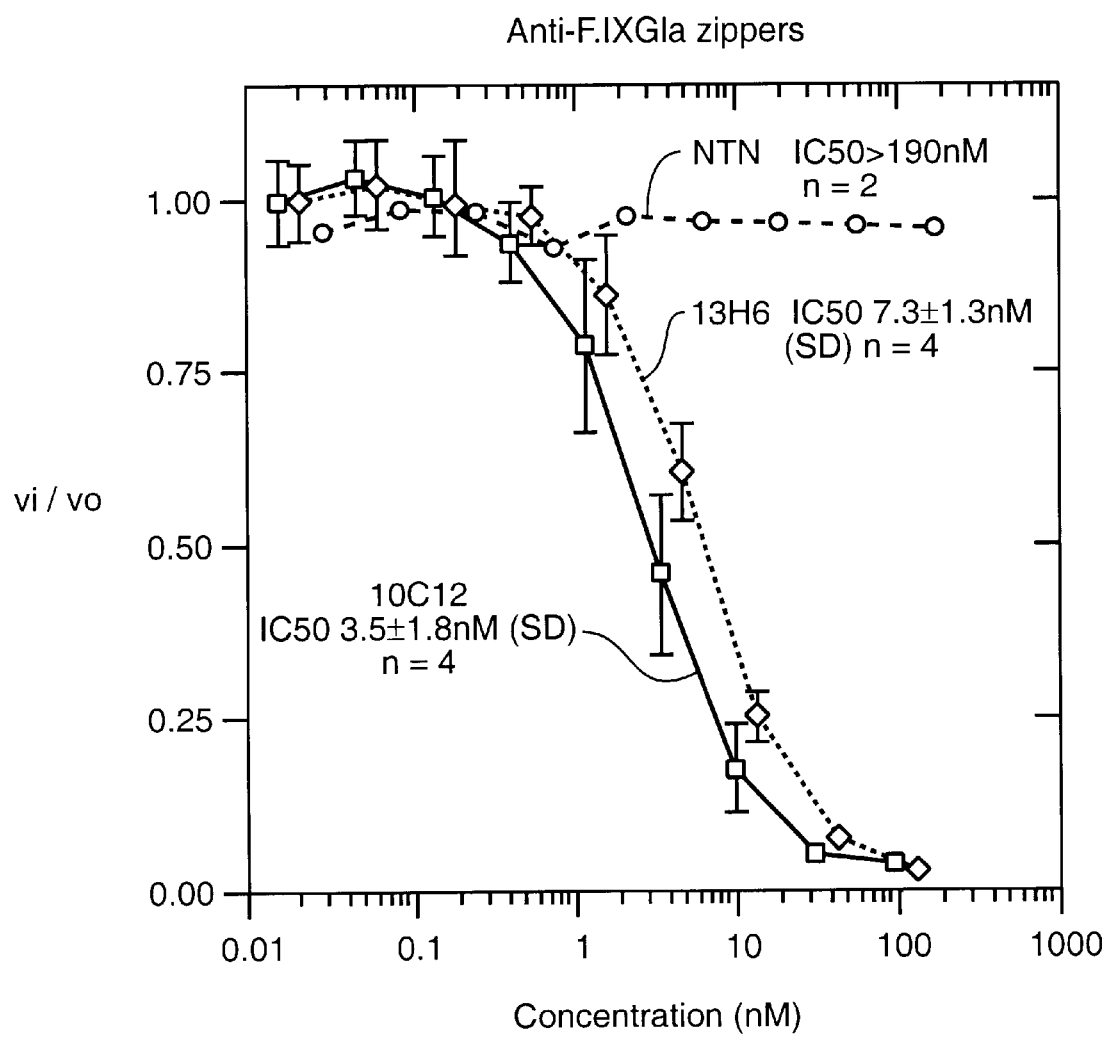
FIG._8

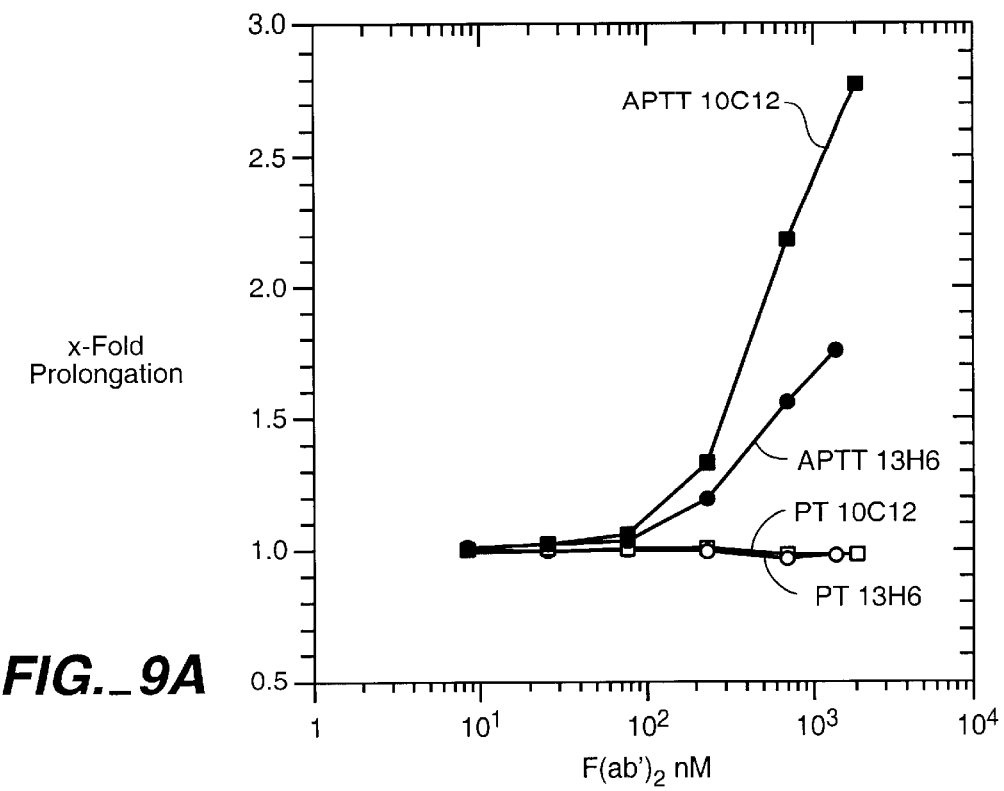
FIG._9A
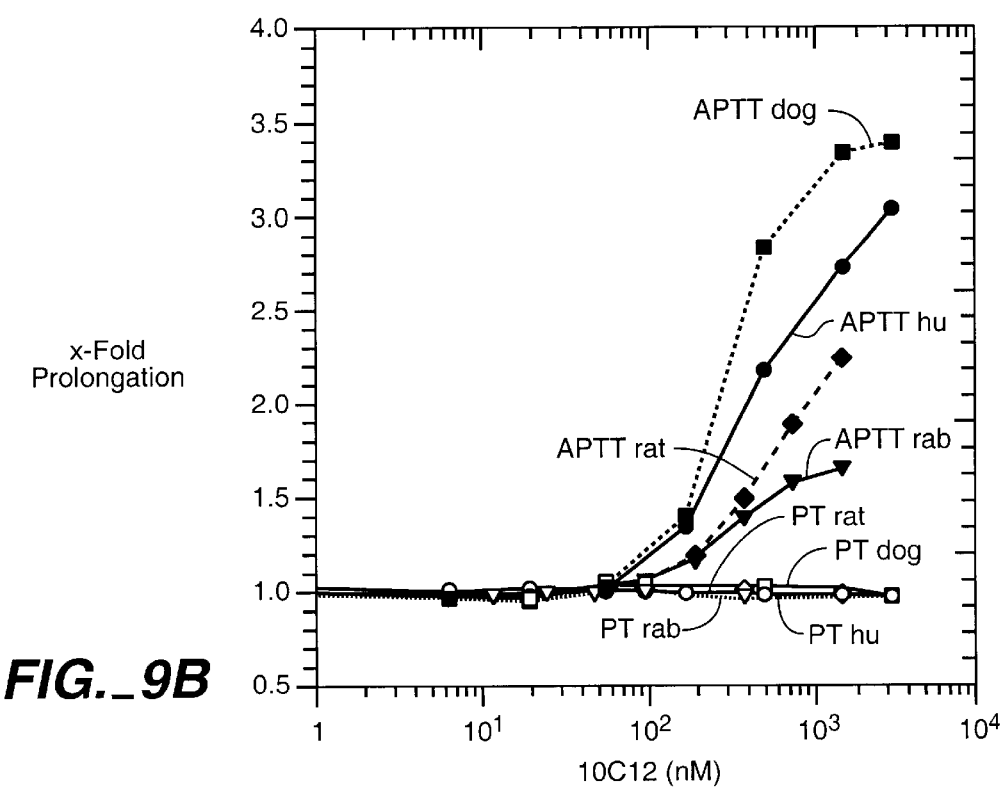
FIG._9B

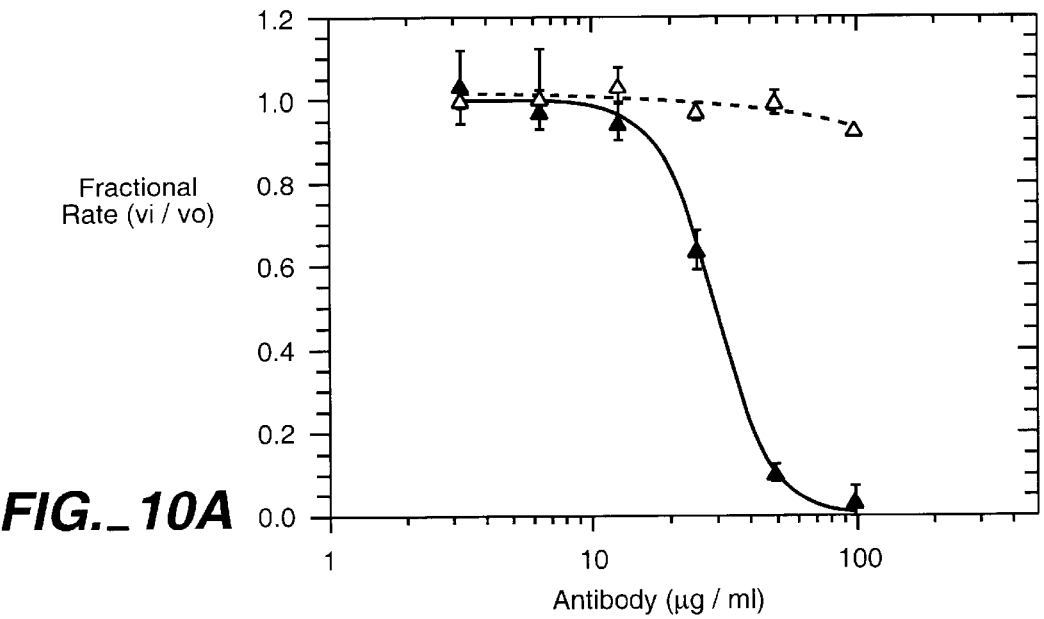
FIG._10A
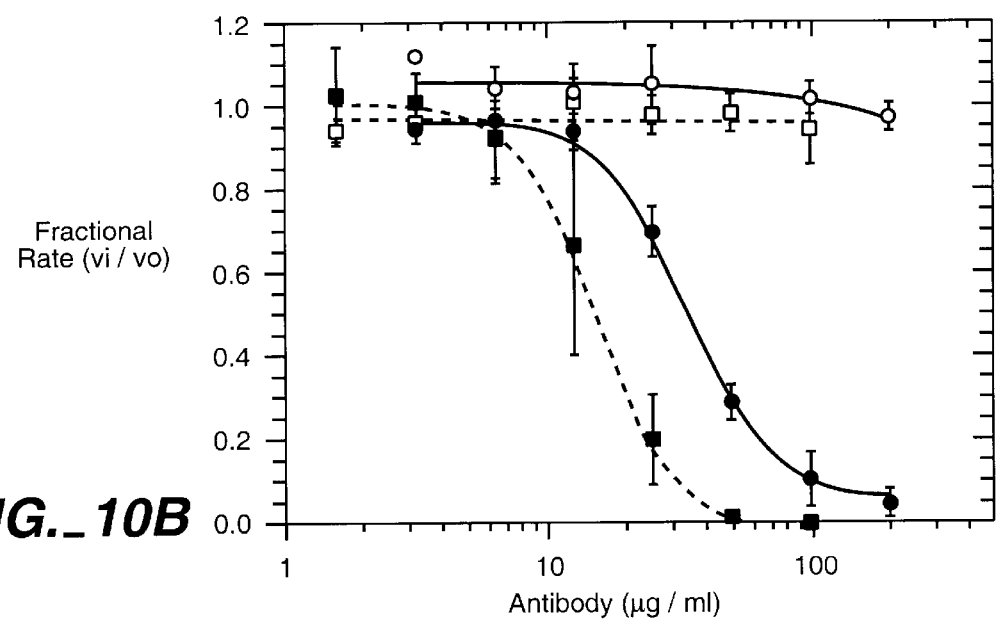
FIG._10B

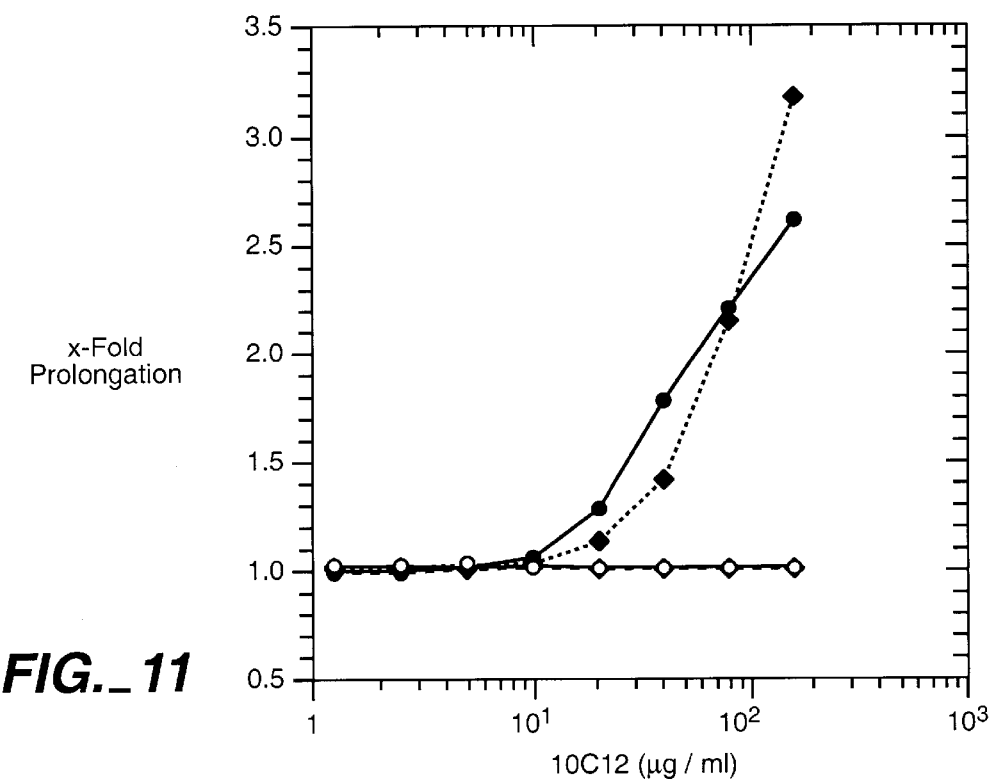
FIG._11
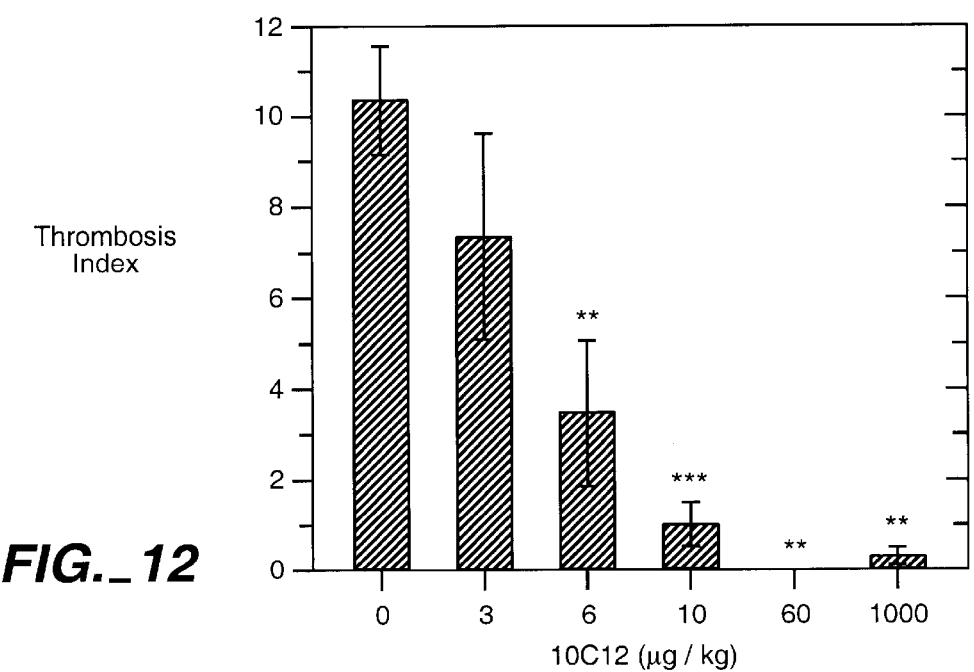
FIG._12

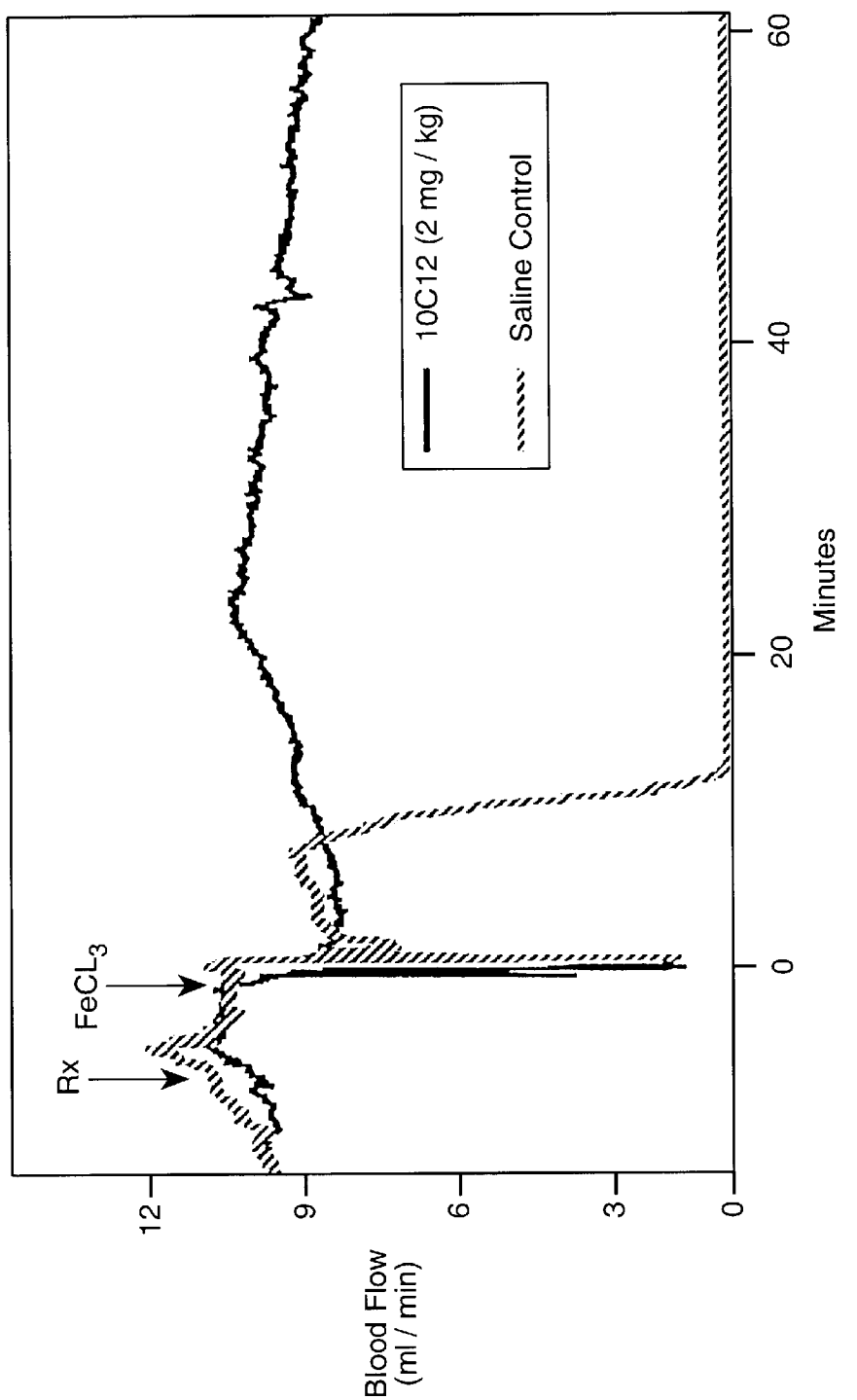
FIG._13

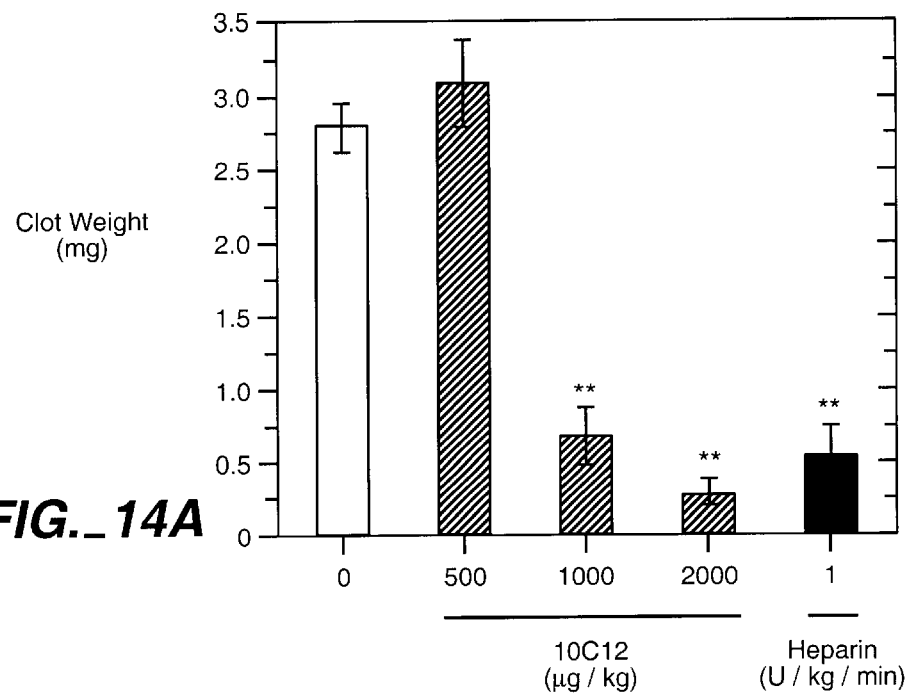
FIG._14A
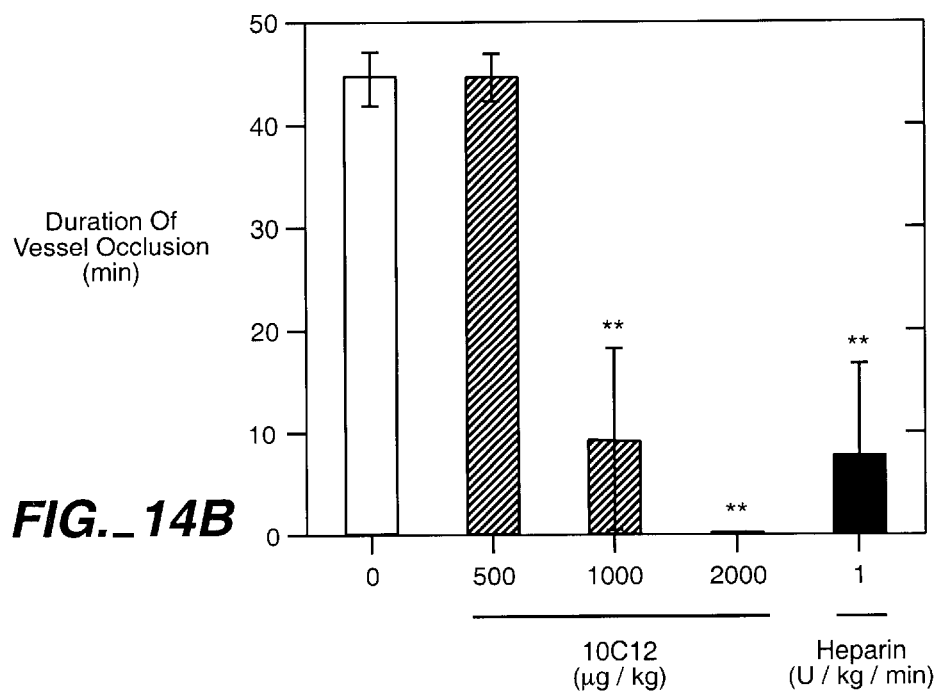
FIG._14B

SEQUENCE LISTING

<160> NUMBER OF SEQ ID NOS: 32

<210> SEQ ID NO 1
<211> LENGTH: 5
<212> TYPE: PRT
<213> ORGANISM: Artificial sequence
<220> FEATURE:
<223> OTHER INFORMATION: Artificial linker sequence for assembling
      single chain antibodies

<400> SEQUENCE: 1

Gly Gly Gly Gly Ser
 1               5

<210> SEQ ID NO 2
<211> LENGTH: 43
<212> TYPE: PRT
<213> ORGANISM: Canis familiaris

<400> SEQUENCE: 2

Tyr Asn Ser Gly Lys Leu Glu Glu Phe Val Arg Gly Asn Leu Glu
 1               5                  10                  15

Arg Glu Cys Ile Glu Glu Lys Cys Ser Phe Glu Glu Ala Arg Glu
                20                  25                  30

Val Phe Glu Asn Thr Glu Lys Thr Thr Glu Phe Trp Lys
                35                  40          43

<210> SEQ ID NO 3
<211> LENGTH: 43
<212> TYPE: PRT
<213> ORGANISM: Mus musculus

<400> SEQUENCE: 3

Tyr Asn Ser Gly Lys Leu Glu Glu Phe Val Arg Gly Asn Leu Glu
 1               5                  10                  15

Arg Glu Cys Ile Glu Glu Arg Cys Ser Phe Glu Glu Ala Arg Glu

-continued

```
                20                  25                  30
Val Phe Glu Asn Thr Glu Lys Thr Thr Glu Phe Trp Lys
                35                  40          43

<210> SEQ ID NO 4
<211> LENGTH: 43
<212> TYPE: PRT
<213> ORGANISM: Oryctolagus cuniculus

<400> SEQUENCE: 4

Tyr Asn Ser Gly Lys Leu Glu Glu Phe Val Ser Gly Asn Leu Glu
 1               5                  10                  15
Arg Glu Cys Ile Glu Glu Arg Cys Ser Phe Glu Glu Ala Arg Glu
                20                  25                  30
Val Phe Glu Asn Thr Glu Lys Thr Thr Glu Phe Trp Lys
                35                  40          43

<210> SEQ ID NO 5
<211> LENGTH: 43
<212> TYPE: PRT
<213> ORGANISM: Homo sapiens

<400> SEQUENCE: 5

Tyr Asn Ser Gly Lys Leu Glu Glu Phe Val Gln Gly Asn Leu Glu
 1               5                  10                  15
Arg Glu Cys Met Glu Glu Lys Cys Ser Phe Glu Glu Ala Arg Glu
                20                  25                  30
Val Phe Glu Asn Thr Glu Arg Thr Thr Glu Phe Trp Lys
                35                  40          43

<210> SEQ ID NO 6
<211> LENGTH: 42
<212> TYPE: PRT
<213> ORGANISM: Homo sapiens

<400> SEQUENCE: 6

Ala Asn Ser Lys Leu Glu Glu Met Lys Lys Gly His Leu Glu Arg
 1               5                  10                  15
Glu Cys Met Glu Glu Thr Cys Ser Tyr Glu Glu Ala Arg Glu Val
                20                  25                  30
Phe Glu Asp Ser Asp Lys Thr Asn Glu Phe Trp Asn
                35                  40      42

<210> SEQ ID NO 7
<211> LENGTH: 42
<212> TYPE: PRT
<213> ORGANISM: Homo sapiens

<400> SEQUENCE: 7

Ala Asn Ala Lys Leu Glu Glu Leu Arg Pro Gly Ser Leu Glu Arg
 1               5                  10                  15
Glu Cys Lys Glu Glu Gln Cys Ser Phe Glu Glu Ala Arg Glu Ile
                20                  25                  30
Phe Lys Asp Ala Glu Arg Thr Lys Leu Phe Trp Ile
                35                  40      42

<210> SEQ ID NO 8
<211> LENGTH: 42
<212> TYPE: PRT
<213> ORGANISM: Homo sapiens
```

-continued

```
<400> SEQUENCE: 8

Ala Asn Ser Lys Leu Glu Glu Leu Arg His Ser Ser Leu Glu Arg
 1               5                  10                  15

Glu Cys Ile Glu Glu Ile Cys Asp Phe Glu Ala Lys Glu Ile
             20                  25                  30

Phe Gln Asn Val Asp Asp Thr Leu Ala Phe Trp Ser
             35                  40      42

<210> SEQ ID NO 9
<211> LENGTH: 42
<212> TYPE: PRT
<213> ORGANISM: Homo sapiens

<400> SEQUENCE: 9

Ala Asn Thr Lys Leu Glu Glu Val Arg Lys Gly Asn Leu Glu Arg
 1               5                  10                  15

Glu Cys Val Glu Glu Thr Cys Ser Tyr Glu Glu Ala Phe Glu Ala
             20                  25                  30

Leu Glu Ser Ser Thr Ala Thr Asp Val Phe Trp Ala
             35                  40      42

<210> SEQ ID NO 10
<211> LENGTH: 5
<212> TYPE: PRT
<213> ORGANISM: Homo sapiens

<400> SEQUENCE: 10

Thr Tyr Ala Met His
 1               5

<210> SEQ ID NO 11
<211> LENGTH: 17
<212> TYPE: PRT
<213> ORGANISM: Homo sapiens

<400> SEQUENCE: 11

Ile Ile Ser Tyr Asp Gly Ser Lys Lys Tyr Tyr Ala Asp Ser Val
 1               5                  10                  15

Lys Gly
    17

<210> SEQ ID NO 12
<211> LENGTH: 11
<212> TYPE: PRT
<213> ORGANISM: Homo sapiens

<400> SEQUENCE: 12

Ala Ser Ile Ala Ala Ala Arg Val Leu Asp Tyr
 1               5                  10  11

<210> SEQ ID NO 13
<211> LENGTH: 13
<212> TYPE: PRT
<213> ORGANISM: Homo sapiens

<400> SEQUENCE: 13

Ser Gly Ser Thr Ser Asn Ile Gly Asn Asn Tyr Val Ser
 1               5                  10      13

<210> SEQ ID NO 14
<211> LENGTH: 7
<212> TYPE: PRT
```

<213> ORGANISM: Homo sapiens

<400> SEQUENCE: 14

Asp Val Ser Lys Arg Pro Ser
 1               5       7

<210> SEQ ID NO 15
<211> LENGTH: 11
<212> TYPE: PRT
<213> ORGANISM: Homo sapiens

<400> SEQUENCE: 15

Ala Ala Trp Asp Asp Ser Leu Ser Glu Phe Leu
 1               5                  10  11

<210> SEQ ID NO 16
<211> LENGTH: 17
<212> TYPE: PRT
<213> ORGANISM: Homo sapiens

<400> SEQUENCE: 16

Val Ile Ser Tyr Asp Gly Ser Asn Lys Tyr Tyr Ala Asp Ser Val
 1               5                  10                  15
Lys Gly
     17

<210> SEQ ID NO 17
<211> LENGTH: 11
<212> TYPE: PRT
<213> ORGANISM: Homo sapiens
<220> FEATURE:
<221> NAME/KEY: unknown
<222> LOCATION: 7
<223> OTHER INFORMATION: unknown amino acid

<400> SEQUENCE: 17

Ser Asp Tyr Gly Gly Asn Xaa Leu Gly Glu Phe
 1               5                  10  11

<210> SEQ ID NO 18
<211> LENGTH: 17
<212> TYPE: PRT
<213> ORGANISM: Homo sapiens

<400> SEQUENCE: 18

Ile Ile Ser Tyr Asp Gly Ser Asn Lys Tyr Tyr Ala Asp Ser Val
 1               5                  10                  15
Lys Gly
     17

<210> SEQ ID NO 19
<211> LENGTH: 11
<212> TYPE: PRT
<213> ORGANISM: Homo sapiens

<400> SEQUENCE: 19

Ala Ser Ile Ala Ala Gly Arg Val Leu Asp Tyr
 1               5                  10  11

<210> SEQ ID NO 20
<211> LENGTH: 17
<212> TYPE: PRT
<213> ORGANISM: Homo sapiens

<400> SEQUENCE: 20

Ile Ile Ser Tyr Asp Gly Ser Lys Lys Tyr Tyr Ala Asp Ser Val
 1               5                  10                 15

Lys Ser
     17

<210> SEQ ID NO 21
<211> LENGTH: 5
<212> TYPE: PRT
<213> ORGANISM: Homo sapiens

<400> SEQUENCE: 21

Ser Tyr Ala Met His
 1           5

<210> SEQ ID NO 22
<211> LENGTH: 17
<212> TYPE: PRT
<213> ORGANISM: Homo sapiens

<400> SEQUENCE: 22

Val Ile Ser His Asp Gly Gly Lys Lys Glu Tyr Ala Asp Ser Val
 1               5                  10                 15

Arg Gly
     17

<210> SEQ ID NO 23
<211> LENGTH: 11
<212> TYPE: PRT
<213> ORGANISM: Homo sapiens

<400> SEQUENCE: 23

Ala Ala Tyr Thr Ala Ala Thr Ile Ala Asp Asn
 1               5                  10  11

<210> SEQ ID NO 24
<211> LENGTH: 10
<212> TYPE: PRT
<213> ORGANISM: Homo sapiens

<400> SEQUENCE: 24

Thr Gly Ser Ser Arg Asp Val Asp Val Ser
 1               5                  10

<210> SEQ ID NO 25
<211> LENGTH: 7
<212> TYPE: PRT
<213> ORGANISM: Homo sapiens

<400> SEQUENCE: 25

Glu Val Ser Lys Arg Pro Ser
 1               5       7

<210> SEQ ID NO 26
<211> LENGTH: 10
<212> TYPE: PRT
<213> ORGANISM: Homo sapiens

<400> SEQUENCE: 26

Ser Ser Tyr Gly Gly Ser Asn Asn Val Val
 1               5                  10

<210> SEQ ID NO 27
<211> LENGTH: 5

-continued

<210> SEQ ID NO 27
<211> LENGTH: 5
<212> TYPE: PRT
<213> ORGANISM: Homo sapiens

<400> SEQUENCE: 27

Asp Tyr Ala Met His
  1               5

<210> SEQ ID NO 28
<211> LENGTH: 17
<212> TYPE: PRT
<213> ORGANISM: Homo sapiens

<400> SEQUENCE: 28

Thr Ile Ser Pro Ser Gly Arg Ser Thr Tyr Asn Ala Asp Ser Val
  1               5                  10                  15

Lys Gly
     17

<210> SEQ ID NO 29
<211> LENGTH: 11
<212> TYPE: PRT
<213> ORGANISM: Homo sapiens

<400> SEQUENCE: 29

Arg Gly Ile Gly Tyr Lys Gly Gly Phe Asp Val
  1               5                  10  11

<210> SEQ ID NO 30
<211> LENGTH: 13
<212> TYPE: PRT
<213> ORGANISM: Homo sapiens

<400> SEQUENCE: 30

Ser Gly Gly Arg Ser Asn Ile Gly Ser Asn Thr Val Lys
  1               5                  10          13

<210> SEQ ID NO 31
<211> LENGTH: 7
<212> TYPE: PRT
<213> ORGANISM: Homo sapiens

<400> SEQUENCE: 31

Gly Asn Asp Gln Arg Pro Ser
  1               5       7

<210> SEQ ID NO 32
<211> LENGTH: 12
<212> TYPE: PRT
<213> ORGANISM: Homo sapiens

<400> SEQUENCE: 32

Gln Ser Tyr Asp Ser Ser Leu Arg Gly Ser Arg Val
  1               5                  10      12

HUMAN ANTI-FACTOR IX/IXA ANTIBODIES

The present application claims the benefit of priority under 35 U.S.C. §119 to provisional application No. 60/122,767 filed Mar. 3, 1999 and 60/098,233 filed Aug. 28, 1998, both of which are abandoned.

BACKGROUND OF THE INVENTION

1. Field of the Invention

The present invention relates to isolation, identification, synthesis, expression and purification of antibodies reactive with factor IX (FIX)/factor IXa (FIXa) and especially the FIX/FIXa Gla domain. In particular aspects, the invention provides human antibodies reactive with the human FIX/FIXa Gla domain. The invention further relates to compositions, especially pharmaceutical compositions, articles of manufacture, and methods of inhibiting the activation of FIX/FIXa and inhibiting FIX/FIXa dependent coagulation.

2. Description of Related Disclosures

Factor IXa is a vitamin K dependent plasma serine protease that participates in both the intrinsic and extrinsic pathways of blood coagulation. The $NH_2$ terminal 43 amino acids (Gla domain) of factor IXa and its zymogen factor IX contain 12 Gla residues formed by the vitamin K-dependent carboxylation of Glu residues. The Gla domain is followed by two epidermal growth factor (EGF) type domains, followed by a carboxy terminal serine protease domain.

The Gla domain of FIX/FIXa contains important structural determinants for interaction with high affinity binding sites on vascular endothelial cells and platelets (Heimark et al., (1983) Biochem. Biophys. Res. Commun. 111:723–731; Ahmad et al., (1994) Biochem. 33:12048–12055; Ryan et al., (1989) J. Biol. Chem. 264:20283–20287; Toomey et al., (1992) Biochemistry 31:1806–1808; Cheung et al., (1992) J. Biol. Chem. 267:20529–20531; Rawala-Sheikh et al., (1992) Blood 79:398–405; Cheung et al., (1996) Proc. Natl. Acad. Sci. USA 93:11068–11073; Prorok et al., (1996) Int. J. Pept. Prot. Res. 48:281–285; Ahmad et al., (1998) Biochemistry 37:1671–1679). In the presence of $Ca++$ and $Mg++$ the FIX/FIXa Gla domain adopts different conformations. Coagulation reactions, such as FIX/FIXa-mediated activation of FX proceed with high efficiency on the surface of activated platelets (Ahmad and Walsh (1994) Trends Cardiovasc. Med., 4:271–277).

Antibodies that bind the FIX/FIXa Gla domain have been shown to inhibit FIX/FIXa function, such as cell binding (Cheung et al., (1996) supra; clotting activity (Sugo et al., (1990) Thromb. Res. 58:603–614) and FIX/FIXa activation by FXI (Sugo et al., (1990) supra; Liebman et al., (1987) J. Bio. Chem. 262:7605–7612). Rabbit and murine antibodies to FIX/FIXa have been shown to bind to the C- and N-terminal region of the Gla domain (Liebman et al., (1993) Eur. J. Biol. Chem. 212:339–345 and Sugo et al., (1990) Thromb. Res. 58:603–614). Antibodies reactive with human FIX/IXa have been shown to inhibit the activation of FIX to FIXa and inhibit coagulation in a FIXa dependent assay (Blackburn et al., (1997) Blood 90: Suppl. 1:424–425a). Active site inhibited FIXa attenuates thrombosis in vivo (Wong et al., (1997) Thromb. Haemost. 77:1143–1147; Benedict et al., (1991) J. Clin. Invest. 88:1760–1765; Spanier et al., (1998) J. Thoracic Cardiovasc. Surgery 115:1179–1188).

SUMMARY OF THE INVENTION

The present invention provides isolated antibodies, antibody fragments, especially human antibodies and antibody fragments, reactive with the factor IX or factor IXa Gla domain. In preferred aspects the antibodies or antibody fragments inhibit an activity associated with blood coagulation factor IX or IXa. Advantageously, the antibodies of the present invention provide for the preparation of potent pharmaceutical compositions comprising the antibodies. The pharmaceutical compositions provide for low dose pharmaceutical formulations for the treatment of acute and chronic thrombotic disorders without compromising normal hemostasis.

In one embodiment, the invention provides an antibody or antibody fragment that reacts with human factor FIX/FIXa and especially the human FIX/FIXa Gla domain. Representative antibody fragments include Fv, scFv, Fab, $F(ab')_2$ fragments, as well as diabodies and linear antibodies. These fragments may be fused to other sequences including, for example, a "leucine zipper" or other sequence and include pegylated sequences or Fc variants used to improve or modulate half-life. Representative antibodies or antibody fragments comprise three complementarity-determining regions (CDRs) referred to herein as CDR1, CDR2 and CDR3. The amino acid sequences of the CDR polypeptides are selected from those of the exemplary antibody fragments 10C12, 11C5, 11G9, 13D13H6 and 14H9 and variants thereof. Preferred antibodies are selected from the group consisting of Ab1, Ab2, Ab3, Ab4, Ab5 and Ab6, wherein the CDRs of Ab1–Ab6 correspond to those of 10C12, 11C5, 11G9, 13D1, 13H6 and 14H9, respectively.

In one embodiment, the composition of the present invention is an antibody polypeptide and the invention encompasses a composition of matter comprising an isolated nucleic acid, preferably DNA, encoding the polypeptide of the invention. According to this aspect, the invention further comprises an expression control sequence operably linked to the DNA molecule, an expression vector, preferably a plasmid, comprising the DNA molecule, where the control sequence is recognized by a host cell comprising the vector, as well as a host cell comprising the vector.

The present invention further extends to therapeutic applications for the antibody compositions described herein. Thus the invention includes a pharmaceutical composition comprising a pharmaceutically acceptable excipient and an antibody or antibody fragment of the invention. The invention includes kits and articles of manufacture comprising the antibody compositions of the invention. Kits and articles of manufacture preferably include:

(a) a container;

(b) a label on said container; and (C) a composition comprising an antibody or antibody fragment of the invention contained within said container; wherein the composition is effective for treating a coagulation disorder and the optional label on said container indicates that the composition can be used for treating a coagulopathic disorder. The kits optionally include accessory components such as a second container comprising a pharmaceutically-acceptable buffer and instructions for using the composition to treat a coagulation related disorder.

Pharmaceutical compositions comprising the antibodies or antibody fragments can be used in the treatment or prophylaxis of thrombotic or coagulopathic diseases or disorders and include, for example, methods of treating a mammal for which inhibiting a FIX/FIXa mediated event is indicated. The methods comprise administering a therapeutically effective amount of a pharmaceutical composition of the invention to the mammal. Such indications include, deep venous thrombosis, arterial thrombosis, unstable angina, post myocardial infarction, post surgical thrombosis, coronary artery bypass graft (CABG), percutaneous transluminal coronary angioplasty (PTCA), stroke, tumor growth, invasion or metastasis, inflammation, septic shock, hypotension, ARDS, atrial fibrillation and DIC. The compositions of the present invention may also be used as an adjunct in thrombolytic therapy.

BRIEF DESCRIPTION OF THE DRAWINGS

FIGS. 1A and 1B: Gla domain sequences. Sequence homology between. FIX Gla domains from various species: human, SEQ ID NO:5; canine, SEQ ID NO:2; murine, SEQ ID NO:3 and rabbit, SEQ ID NO:4 (FIG. 1A) and Gla domains of various human coagulation proteins: factor IX, SEQ ID NO:5; factor X, SEQ ID NO:6; factor VII, SEQ ID NO:7; protein C, SEQ ID NO:8 and prothrombin, SEQ ID NO:9 (FIG. 1B). Non-homologous residues are indicated in bold face type.

FIG. 2: V-gene segment usage and CDR sequences of selected scFv. Residues different from those of 10C12 are indicated in bold type. 10C12 heavy chain: CDR1, SEQ ID NO:10; CDR2, SEQ ID NO:11, CDR3, SEQ ID NO:12. 10C12 light chain: CDR1, SEQ ID NO:13; CDR2, SEQ ID NO:14; CDR3, SEQ ID NO:15. 11C5 heavy chain: CDR1, SEQ ID NO:10; CDR2, SEQ ID NO:16; CDR3, SEQ ID NO: 17. 11C5 light chain: CDR1, SEQ ID NO:13; CDR2, SEQ ID NO:14; CDR3, SEQ ID NO:15. 11G9 heavy chain: CDR1, SEQ ID NO:10; CDR2, SEQ ID NO:18; CDR3, SEQ ID NO:19. 11G9 light chain: CDR1, SEQ ID NO:13; CDR2, SEQ ID NO:14; CDR3, SEQ ID NO:15. 13D1 heavy chain: CDR1, SEQ ID NO:10; CDR2, SEQ ID NO:20; CDR3, SEQ ID NO:12. 13D1 light chain: CDR1, SEQ ID NO:13; CDR2, SEQ ID NO:14; CDR3, SEQ ID NO:15. 13H6 heavy chain: CDR1, SEQ ID NO:21; CDR2, SEQ ID NO:22; CDR3, SEQ ID NO:23. 13H6 light chain: CDR1, SEQ ID NO:24; CDR2, SEQ ID NO:25; CDR3, SEQ ID NO:26. 14H9 heavy chain: CDR1, SEQ ID NO:27; CDR2, SEQ ID NO:28; CDR3, SEQ ID NO:29. 14H9 light chain: CDR1, SEQ ID NO:30; CDR2, SEQ ID NO:31; CDR3, SEQ ID NO:32.

FIG. 3: Affinities of selected anti-FIX F(ab')$_2$ for human FIX/FIXa: Human FIX was coupled to a biosensor chip according to supplier's description (BIAcore Inc., Piscataway N.J.). The affinities were calculated from the measured association and dissociation constants using a BIAcore-2000™ surface plasmon resonance system (Pharmacia Biosensor).

FIG. 4: Binding of scFv to full length FIX. Plates were coated with 10 μg/ml of 9E10 anti-C-myc mAb. Serial dilutions of scFv (10 μg/ml to 5 ng/ml) were added to each well for one hour followed by biotinylated factor IX (1 μg/ml) and streptavidin-HRP.

FIGS. 5A and 5B: Effect of scFv on FIX binding to bovine aortic endothelial cells and on platelet-dependent coagulation. In FIG. 5A assays were conducted at 4° C. in 100 μl 10 mM Hepes, 137 mM NaCl, 4 mM KCl, 11 mM glucose, 2 mM CaCl$_2$, 5 mg/ml bovine serum albumin pH 7.5 (assay buffer). Monolayers of bovine aortic endothelial (BAE) cells were washed once with assay buffer without CaCl$_2$ before use. The scFv were pre-incubated with biotinylated human FIX in 100 μl buffer for one hour, then added to BAE cells for two hours, washed and incubated with 100 μl of 3,3'5, 5'-tetramethylbenzidine/H$_2$O$_2$ (Kirkgaard & Perry) substrate for ten minutes. The reaction was quenched with 100 μl of 1M H$_3$PO$_4$ and the optical density was read at 450 nm. FIG. 5B—Washed human platelets were activated by adenosine diphosphate (ADP) and allowed to adhere to collagen type III before scFv and human recalcified platelet poor plasma were added. The effect on coagulation was monitored over 90 min. by measuring the increase of the optical density at 405 nm. Shown are the effects of the scFv at a plasma concentration of 500 nM.

FIGS. 6A and 6B: Binding specificity of anti-FIX scFv and F(ab')$_2$. Elisa plates were coated with factor IX, factor X, factor VII, prothrombin, or protein C at 1 μg/ml. ScFv (FIG. 6A) and F(ab')$_2$ (FIG. 6B) were added at 5 μg/ml and 0.02 μg/ml, respectively, for one hour. This step was followed by addition of biotinylated 9E10 anti-C-myc mAb (2 μg/ml) and then streptavidin-HRP. Factor IX+serum: scFvs were preincubated for 1 hour on ice with FIX-deficient serum (less than 1% Factor IX residual activity) prior to incubation with FIX coated on plate. All ELISA buffers contained 2 mM CaCl$_2$.

FIGS. 7A and 7B. Comparison of two anti-FIX-F(ab')$_2$-leu zipper fragments in platelet-dependent coagulation assay. Collagen-adherent activated human platelets were incubated with different concentrations of 10C12 F(ab')$_2$-leu zipper (FIG. 7A) and 13H6 F(ab')$_2$-leu zipper (FIG. 7B) and recalcified human plasma was added to start the coagulation process. Six different concentrations per antibody were tested, three of which are shown in each graph. Each value represents the mean ±SD of 3 independent experiments. The IC50 values were calculated from inhibition curves, using the OD values at the 100 min. time point with the control value (uninhibited coagulation) set at 100%. 10C12, IC50= 59±3 nM; 13H6, IC50=173±43 nM. Open circles: 1000 nM, open squares: 250 nM, diamonds:62.5 nM, filled triangles: 15.6 nM, filled circles: control.

FIG. 8. Inhibition of FIXa-dependent activation of FX by anti-FIX F(ab')$_2$-leu zipper. Antibodies were incubated with FIXa, FVIIIa and phospholipids for 20 min. after which FX was added. The rate of FXa generation was calculated after measuring the concentration of FXa at different time points using the chromogenic substrate S2765. The inhibition by antibodies is expressed as fractional rates (inhibited divided by uninhibited rates of FXa generation). The concentrations of antibodies 10C12 (squares), 13H6 (diamonds) and an irrelevant control antibody anti-Neurturin (circles) are those in the final reaction mixture with FX.

FIGS. 9A and 9B. Effects of 10C12 F(ab')$_2$-leu zipper on activated partial thromboplastin time (APTT) and prothrombin time (PT). In FIG. 9A the antibodies were incubated with human plasma for 10 min. at 37° C. and the APTT and PT were measured on an ACL 300. Shown are the APTT (filled symbols) and PT (open symbols) by 10C12 F(ab')$_2$-leu zipper (squares) and 13H6 F(ab')$_2$-leu zipper (circles). In FIG. 9B 10C12 F(ab')$_2$-leu zipper was incubated for 10 min. at 37° C. with plasma of different species and the APTT and PT were measured on an ACL 300. Shown are the APTT (filled symbols) and PT (open symbols) of human (circles), rat (diamonds), dog (squares) and rabbit plasma (inverted triangles).

FIGS. 10A and 10B: FIX activation by FXIa and by the tissue factor:factor VIIa (TF:FVIIa) complex. FIX (400 nM) was incubated with 10C12 (filled symbols) or a control antibody (NTN: anti-neurturin) (open symbols) in HBSA-5 mM CaCl$_2$. FIG. 10A: 1 nM FXIa was added to start the reaction. FIG. 10B: relipidated TF:FVIIa (4 nM: 1 nM) (circles) or membrane TF:FVIIa (150 μg/ml: 1 nM) (squares) was added to start the reaction. At defined time intervals reaction aliquots were quenched in EDTA-ethyleneglycol and FIXa amdiolytic activity in each sample was determined after adding FIXa substrate #299. The inhibition of the rates of FIXa generation were expressed as fractional rates (vi/vo)±SD of 3–4 independent experiments.

FIG. 11: Measurement of activated partial thromboplastin time (APTT) and prothrombin time (PT) in plasma of guinea pig and rat. 10C12 was diluted in citrated plasma of guinea pig and rat. After an incubation of 10 min., human relipidated tissue factor (Innovin) or Actin FS were added to start the PT (open symbols) and APTT (filled symbols) reaction, respectively. The effects on clotting were expressed as fold prolongation of control plasma clotting times diamonds= guinea pig; circles=rat.

FIG. 12: Effects of 10C12 on cyclic flow variations (CFVs) in guinea pig arterial thrombosis model. 10C12 and controls were given by intravenous bolus administration 15 min. prior to the initiation of CFVs in the carotid artery. The number of CFVs during a 40 min. period was recorded and the thrombosis index calculated as the ratio of CFVs divided by the number of applied pinches. $p \leq 0.01$, *$p \leq 0.001$ versus control by Mann-Whitney U-test following determination of significant differences between multiple groups in Kruskal-Wallis test.

FIG. 13: Effect of $FeCl_3$ treatment on carotid artery blood flow in the rat. Representative carotid artery blood flow tracings in rats treated with either saline or 10C12 prior to placement of a $FeCl_3$ saturated disc. Occlusive thrombosis was induced in 10 of 10 control treated rats and 0 of 5 rats treated with an iv bolus of 2 mg/kg of 10C12.

FIGS. 14A and 14B: Effects of 10C12 and heparin on thrombus formation in the $FeCl_3$-induced arterial thrombosis model in the rat. 10C12 and controls were given as bolus and heparin-as a 100U/kg bolus followed by infusion at a rate of 1U/kg/min 5 min prior to the placement of the $FeCl_3$-disc onto the exposed artery. FIG. 14A: The effects on clot weight were quantified by removing and weighing the thrombus 65 min. after drug administration started. FIG. 14B: Effects on the duration of vessel occlusion were determined by measuring the time periods during which zero-flow occurred following placement of the $FeCl_3$-disc. **$p^2 0.01$ versus control by Mann-Whitney U-test following determination of significant differences between multiple groups in Kruskal-Wallis test.

DETAILED DESCRIPTION OF THE PREFERRED EMBODIMENT DEFINITIONS

Terms used in the claims and specification are defined as set forth below unless otherwise specified.

Abbreviations used throughout the description include: FIX for factor IX; FIXa for factor IXa; FXIa for factor XIa; FXa for factor Xa; TF for tissue factor; FVII for zymogen factor VII; FVIIa for factor VIIa; PT for prothrombin time; APTT for activated partial thromboplastin time.

The term amino acid or amino acid residue, as used herein, refers to naturally occurring L amino acids or to D amino acids as described further below with respect to variants. The commonly used one- and three-letter abbreviations for amino acids are used herein (Bruce Alberts et al., Molecular Biology of the Cell, Garland Publishing, Inc., New York (3d ed. 1994)).

An FIX/FIXa mediated or associated process or event, or equivalently, an activity associated with plasma FIX/FIXa, according to the present invention is any event which requires the presence of FIX/IXa. The general mechanism of blood clot formation is reviewed by Ganong, in Review of Medical Physiology, 13th ed., Lange, Los Altos Calif., pp411–414 (1987); Bach (1988) CRC Crit. Rev. Biochem. 23(4):339–368 and Davie et al., (1991) Biochemistry 30:10363; and the rate of FIX in Limentani et al., (1994) *Hemostasis and Thrombosis Basic Principles and Clinical Practice*, Third Edition, Coleman et al. Eds., Lippincott Company, Philadelphia. Coagulation requires the confluence of two processes, the production of thrombin which induces platelet aggregation and the formation of fibrin which renders the platelet plug stable. The process comprises several stages each requiring the presence of discrete proenzymes and procofactors. The process ends in fibrin crosslienking and thrombus formation. Fibrinogen is converted to fibrin by the action of thrombin. Thrombin, in turn, is formed by the proteolytic cleavage of prothrombin. This proteolysis is effected by FXa which binds to the surface of activated platelets and in the presence of FVa and calcium, cleaves prothrombin. TF-FVIIa is required for the proteolytic activation of FX by the extrinsic pathway of coagulation. FIX is activated by two different enzymes, FXIa (Fujikawa et al., (1974) Biochemistry, 13:4508–4516; Di Scipio et al., (1978) J. Clin. Invest., 61:1528–1538; Østerud et al., (1978) J. Biol. Chem. 253:5946–5951) and the tissue factor:factor VIIa (TF:FVIIa) complex (Østerud and Rapaport (1977) Proc. Natl. Acad. Sci. USA 74:5260–5264). The formed FIXa in complex with its cofactor FVIIIa assembles into the intrinsic Xase complex on cell surfaces such as platelets and endothelial cells, and converts substrate FX into FXa (Mann et al., (1992) Semin. Hematol. 29:213–226). Thrombin generated by FXa enzymatic activity, cleaves fibrinogen leading to fibrin formation and also activates platelets resulting in platelet aggregation. Therefore, a process mediated by or associated with FIX/IXa, or an activity associated with FIXa includes any step in the coagulation cascade from the introduction of FIX in the extrinsic or intrinsic pathway to the formation of a fibrin platelet clot and which initially involves the presence FIX/IXa. FIX/FIXa mediated or associated process, or FIXa activity, can be conveniently measured employing standard assays such as those described herein.

A FIX/FIXa related disease or disorder is meant to include chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, acute and chronic indications such as inflammation, septic shock, septicemia, hypotension, adult respiratory distress syndrome (ARDS), disseminated intravascular coagulopathy (DIC) and other diseases.

The term "FIX" is used to refer to a polypeptide having an amino acid sequence corresponding to a naturally occurring mammalian factor IX or a recombinant IX described below. Naturally occurring FIX includes human species as well as other animal species such as rabbit, rat, porcine, non human primate, equine, murine, and bovine FIX (see, for example, Yoshitake et al., (1985) Biochemistry 24:3736 (human)). The amino acid sequence of the mammalian factor IX/IXa proteins are generally known or obtainable through conventional techniques. The 43 amino acid γ-carboxyglutamic acid (Gla) domains of human, canine, murine and rabbit FIX are listed in FIG. 1.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. Further, administration of the agent after onset and after clinical symptoms have developed where administration affects clinical parameters of the disease or disorder and perhaps amelioration of the disease, comprises "treatment" of the disease.

Those "in need of treatment" include mammals, such as humans, already having the disease or disorder, including those in which the disease or disorder is to be prevented.

Antibodies or immunoglobulins are, most commonly, heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al. (1985), J. Mol. Biol. 186:651; Novotny and Haber (1985), Proc. Natl. Acad. Sci. U.S.A. 82:4592).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991), Sequences of Proteins of Immunological Interest, Fifth Edition, National Institute of Health, Bethesda, Md.). The constant domains are not involved directly in binding an antibody to an antigen, but exhibit various effector functions, such as participation of the antibody in antibody-dependent cellular toxicity.

Papain digestion of antibodies produces two identical antigen-binding fragments, called Fab fragments, each with a single antigen-binding site, and a residual Fc fragment, whose name reflects its ability to crystallize readily. Pepsin treatment yields an F(ab')$_2$ fragment that has two antigen-combining sites and is still capable of cross-linking antigen.

Fv is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in *The Pharmacology of Monoclonal Antibodies*, vol. 113, Rosenburg and Moore eds., Springer-Verlag, New York, pp. 269–315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The light chains of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies) and antibody compositions with polyepitopic specificity.

"Antibody fragments" comprise a portion of an intact antibody, generally the antigen binding site or variable region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multi specific antibodies formed from antibody fragments.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993), Proc. Natl. Acad. Sci. USA 90:6444–6448.

The expression "linear antibodies" when used throughout this application refers to the antibodies described in Zapata et al. (1995) Protein Eng. 8(10):1057–1062. Briefly, these antibodies comprise a pair of tandem Fd segments ($V_H$—$C_{H1}$-$V_H$—$C_H1$) which form a pair of antigen binding regions. Linear antibodies can be bispecific or monospecific.

A "variant" antibody or antibody fragment, refers to a molecule which differs in amino acid sequence from a "parent" antibody or antibody fragment amino acid sequence by virtue of addition, deletion and/or substitution of one or more amino acid residue(s) in the parent antibody or antibody fragment sequence. For example, the variant may comprise one or more amino acid substitution(s) in one or more CDR's of the parent antibody or antibody fragment. For example, the variant may comprise at least one, from about one to about ten, or preferably from about two to about five, amino acid substitutions in one or more CDR's of the parent antibody or antibody fragment. Ordinarily, the variant will have an amino acid sequence having at least 75% amino acid sequence identity with the parent antibody heavy or light chain variable domain sequences, more preferably at least 80%, more preferably at least 85%, more preferably at least 90%, and preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind the human FIX Gla domain and preferably has properties which are superior to those of the parent antibody. For example, the variant may have a greater binding affinity for the human FIX Gla domain when compared with the parent antibody or antibody from which it is derived. In analyzing such properties, a variant antibody or antibody fragment, such as a Fab form of the variant, is compared to the same fragment, for example the Fab form, of the parent antibody or antibody fragment. As a further example, a full length antibody form of the variant should be compared to a full length form of the parent antibody, since it has been found that the format of the antibody or antibody fragment impacts its activity in the biological activity assays disclosed herein. The variant antibody or antibody fragment of particular interest herein is one which displays between 2 and ten fold, preferably, at least about 10 fold, preferably at least about 20 fold, and more preferably at least about 50 fold, enhancement in biological activity when compared to the parent antibody. The term variant is meant to include an antibody or antibody fragment having at least qualitative biological activity in common with a parent antibody or antibody fragment and which has at least one amino acid substitution in at least one CDR of the exemplary CDRs described in FIG. 2. The qualitating biological activity referred to is selected, without limitation to a single activity, from the group consisting of i) reactivity with the human FIX/FIXa Gla domain, ii) inhibition of activation of FIX by FXIa; iii) inhibition of activation of FIX by tissue factor-:factor VIIa complex; and iv) inhibition of FX activation. Assay systems for measurement of inhibition of FIX and FX activation are known in the art. In preferred embodiments, the variant of the present invention competes with a parent antibody or antibody fragments for binding a human FIX/IXa Gla domain. Therefore, without limitation to any one theory, qualitating biological activity may be defined as the ability to compete with a parent antibody or antibody fragment and in preferred embodiments thereby inhibit an activity associated with FIX such as its activation or the activation FX. As will be appreciated from the foregoing, the term "compete" and "ability to compete" are relative terms. Thus the terms, when used to describe the activity of the variant, means a variant that when added in a 10-fold molar excess to a parent antibody or fragment in a standard binding assay produces at least a 50% inhibition of binding of the parent antibody or fragment. Preferably the variant will produce at least a 50% inhibition of binding in a 5-fold molar excess and most preferably at least a 2-fold molar excess. A preferred variant of the present invention will produce at least a 50% inhibition of binding when present in a 1:1 stoichiometric ratio with the parent antibody or antibody fragment.

The "parent" antibody or antibody fragment herein is one which is encoded by an amino acid sequence used for the preparation of the variant. Preferably, the parent antibody or antibody fragment has a human framework region and has human antibody constant region(s). For example, the parent antibody or antibody is preferably an isolated human antibody or fragment thereof.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present ordinarily, however, isolated antibody will be prepared by at least one purification step.

The term "epitope tagged" when used herein refers to an antibody fused to an "epitope tag". The epitope tag polypeptide has enough residues to provide an epitope against which an antibody thereagainst can be made, yet is short enough such that it does not interfere with activity of the antibody. The epitope tag preferably is sufficiently unique so that the antibody thereagainst does not substantially cross-react with other epitopes. Suitable tag polypeptides generally have at least 6 amino acid residues and usually between about 8–50 amino acid residues (preferably between about 9–30 residues). Examples include the flu HA tag polypeptide and its antibody 12CA5 (Field et al. (1988), Mol. Cell. Biol. 8:2159–2165); the c-myc tag and the 8F9, 3C7, 6E10, G4, B7 and 9E10 antibodies thereto (Evan et al. (1985), Mol. Cell. Biol. 5(12):3610–3616); and the Herpes Simplex virus glycoprotein D (gD) tag and its antibody (Paborsky et al. (1990), Protein Engineering 3(6):547–553 (1990)). In certain embodiments, the epitope tag is a "salvage receptor binding epitope". As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

MODES FOR CARRYING OUT THE INVENTION

The invention provides an antibody or antibody fragment comprising a heavy chain variable domain comprising a CDR amino acid sequence of any of the heavy chain polypeptide CDR amino acid sequences of FIG. 2. The invention encompasses a single chain antibody fragment comprising any of the heavy chain CDR sequences, with or without any additional amino acid sequence. By way of example, the invention provides a single chain antibody fragment comprising a heavy chain comprising a CDR1, a CDR2 and a CDR3 without any associated light chain variable domain amino acid sequence, i.e. a single chain species that makes up one half of an Fv fragment.

Further provided herein are an antibody or antibody fragment comprising any of the heavy chain CDR sequences as described above, and further comprising a light chain CDR amino acid sequence comprising the amino acid sequence of a light chain CDR amino acid sequence of FIG. 2. By way of example, in one embodiment, the invention provides a single chain antibody fragment wherein any heavy chain comprising a CDR1 a CDR2 and a CDR3, and light chain (λc) comprising a λc-CDR1, a λc-CDR2 and a λc-CDR3 are contained in a single chain polypeptide species. By way of example and not limitation, the single chain antibody fragment in, a particular embodiment, a scFv species comprising the heavy chain joined to the light chain by means of a flexible peptide linker sequence, wherein the heavy chain and light chain variable domains can associate in a "dimeric" structure analogous to that formed in a two-chain Fv species. In another embodiment, the single chain antibody fragment is a species comprising the heavy chain joined to the light chain by a linker that is too short to permit intramolecular pairing of the two variable domains, i.e., a single chain polypeptide monomer that forms a diabody upon dimerization with another monomer.

In yet another embodiment, the invention provides an antibody fragment comprising a plurality of polypeptide chains, wherein one polypeptide chain comprises any of the heavy chain CDRs of FIG. 2 and a second polypeptide chain comprises any of the light chain CDRs of FIG. 2 and the two polypeptide chains are covalently linked by one or more interchain disulfide bonds. In a preferred embodiment, the foregoing two-chain antibody fragment is selected from the group consisting of Fab, Fab', Fab'—SH, Fv, and $F(ab')_2$.

The invention also provides an antibody or antibody fragment comprising a heavy chain variable domain containing any of the CDRs of FIG. 2 and optionally further comprising a light chain-variable domain containing any of the light chain CDRs of FIG. 2, wherein the heavy chain variable domain, and optionally the light chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al. (supra).

In a preferred embodiment, the antibody or antibody fragment comprises any of the heavy chain CDR amino acid sequences of FIG. 2 in a variable domain that is fused to a heavy chain constant domain containing a leucine zipper sequence. The leucine zipper can increase the affinity and/or production efficiency of the antibody or antibody fragment of interest. Suitable leucine zipper sequences include the jun and fos leucine zippers taught by Kostelney et al. (1992), J. Immunol., 148: 1547–1553, and the GCN4 leucine zipper described in the Examples below. In a preferred embodiment, the antibody or antibody fragment comprises the variable domain fused at its C-terminus to the GCN4 leucine zipper.

The invention additionally encompasses antibody and antibody fragments comprising variant antibody or antibody fragment. Variant antibodies or antibody fragments include any of the foregoing described antibodies or antibody fragments wherein at least one amino acid of a CDR described in FIG. 2 has been substituted with another amino acid. The skilled artisan will recognize that certain of the amino acids of the CDR's described in FIG. 2 may be substituted, modified and in some cases deleted, to provide an antibody or antibody fragment with an improved or altered biological activity. Variants of the complementarity determining regions or variants of variable domains comprising the CDR's of FIG. 2 which exhibit higher affinity for the FIX Gla domain and/or possess properties that yield greater efficiency in recombinant production processes than that of the parent antibody or antibody fragment are preferred in the context of the present invention.

Methods of Making

Nucleic acid encoding the antibodies or antibody fragments of the invention can be prepared from a library of single chain antibodies displayed on a bacteriophage. The preparation of such a library is well known to one of skill in this art. Suitable libraries may be prepared by the methods described in WO 92/01047, WO 92/20791, WO 93/06213, WO 93/11236, WO 93/19172, WO 95/01438 and WO 95/15388. In a preferred embodiment, a library of single chain antibodies (scFv) may be generated from a diverse population of human B-cells from human donors mRNA corresponding to the VH and VL antibody chains is isolated and purified using standard techniques and reverse transcribed to generate a population of cDNA. After PCR amplification, DNA coding for single chain antibodies is assembled using a linker, such as $Gly_4Ser$ (SEQ ID NO:1), and cloned into suitable expression vectors. A phage library is then prepared in which the population of single chain antibodies is displayed on the surface of the phage. Suitable methods for preparing phage libraries have been reviewed and are described in Winter et. al. (1994), Annu. Rev.

Immunol. 12:433–55; Soderlind et. al. (1992), Immunological Reviews 130:109–123; Hoogenboom, Tibtech (February 1997), Vol. 15; Neri et. al. (1995), Cell Biophysics 27:47–61, and the references described therein.

The antibodies of the invention may be selected by immobilizing a FIX Gla domain and then panning a library of human scFv prepared as described above using the immobilized FIX Gla domain to bind antibody. Griffiths et. al. (1993), EMBO-J 12:725–734. The specificity and activity of specific clones can be assessed using known assays. Griffiths et. al.; Clarkson et. al. (1991), Nature 352:642–648. After a first panning step, one obtains a library of phage containing a plurality of different single chain antibodies displayed on phage having improved binding to the FIX Gla domain. Subsequent panning steps provide additional libraries with higher binding affinities. When avidity effects are a problem, monovalent phage display libraries may be used in which less than 20%, preferably less than 10%, and more preferably less than 1% of the phage display more than one copy of an antibody on the surface of the phage. Monovalent display can be accomplished with the use of phagemid and helper phage as described, for example, in Lowman et. al. (1991), Methods: A Companion to Methods in Enzymology 3(3):205–216. A preferred phage is M13 and display is preferably as a fusion protein with coat protein 3 as described in Lowman et. al., supra. Other suitable phage include f1 and fd filamentous phage. Fusion protein display with other virus coat proteins is also known and may be used in this invention. See U.S. Pat. No. 5,223,409.

Amino acid sequence variants of the antibody are prepared by introducing appropriate nucleotide changes into the antibody DNA, or by peptide synthesis. Such variants include, for example, deletions from, and/or insertions into and/or substitutions of, residues within the amino acid sequences of the antibodies of the examples herein. Any combination of deletion, insertion, and substitution is made to arrive at the final construct, provided that the final construct possesses the desired characteristics. The amino acid changes also may alter post-translational processes of the variant antibody, such as changing the number or position of glycosylation sites.

A useful method for identification of certain residues or regions of the antibody that are preferred locations for mutagenesis is called "alanine scanning mutagenesis," as described by Cunningham and Wells (1989), Science 244:1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the FIX Gla domain. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide or PEG which increases the serum half-life of the antibody.

Another type of variant is an amino acid substitution variant. These variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table A under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

| Original Residue | Exemplary Substitutions | Preferred Substitutions |
| --- | --- | --- |
| Ala (A) | Val; leu; ile | val |
| Arg (R) | Lys; gln; asn | lys |
| Asn (N) | Gln; his; asp, lys; arg | gln |
| Asp (D) | Glu; asn | glu |
| Cys (C) | Ser; ala | ser |
| Gln (Q) | Asn; glu | asn |
| Glu (E) | Asp; gln | asp |
| Gly (G) | Ala | ala |
| His (H) | Asn; gln; lys; arg | arg |
| Ile (I) | Leu; val; met; ala; phe; norleucine | leu |
| Leu (L) | Norleucine; ile; val; met; ala; phe | ile |
| Lys (K) | Arg; gln; asn | arg |
| Met (M) | Leu; phe; ile | leu |
| Phe (F) | Leu; val; ile; ala; tyr | tyr |
| Pro (P) | Ala | ala |
| Ser (S) | Thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the variant antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a human antibody). Generally, the resulting variant(s) selected for further development will have improved biological properties relative to the parent antibody from which they are generated. A convenient way for generating such substitutional variants is affinity maturation using phage using methods known in the art. Briefly, several hypervariable region sites (e.g. 3–7 sites) are-mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identified hypervariable region residues contributing significantly to antigen binding. Alternatively, or in addition, it may be beneficial to analyze a crystal structure of the antigen-antibody complex to identify contact points between the antibody and FIX Gla domain. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for 0-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Preferably, the antibodies are prepared by standard recombinant procedures which involve production of the antibodies by culturing cells transfected to express antibody nucleic acid (typically by transforming the cells with an expression vector) and recovering the antibody from the cells of cell culture.

The nucleic acid (e.g., cDNA or genomic DNA) encoding antibody selected as described above is inserted into a replicable vector for further cloning (amplification of the DNA) or for expression. Many vectors are available, and selection of the appropriate vector will depend on (1) whether it is to be used for DNA amplification or for DNA expression, (2) the size of the nucleic acid to be inserted into the vector, and (3) the host cell to be transformed with the vector. Each vector contains various components depending on its function (amplification of DNA or expression of DNA) and the host cell with which it is compatible. The vector components generally include, but are not limited to, one or more of the following: a signal sequence, an origin of replication, one or more marker genes, an enhancer element, a promoter, and a transcription termination sequence.

(i) Signal Sequence Component

The antibody of this invention may be expressed not only directly, but also as a fusion with a heterologous polypeptide, preferably a signal sequence or other polypeptide having a specific cleavage site at the N-terminus of the mature protein or polypeptide. In general, the signal sequence may be a component of the vector, or it may be a part of the antibody DNA that is inserted into the vector. The heterologous signal sequence selected should be one that is recognized and processed (i.e., cleaved by a signal peptidase) by the host cell. For prokaryotic host cells a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase, alpha factor, or acid phosphatase leaders, the C. albicans glucoamylase leader (EP 362,179 published Apr. 4, 1990), or the signal described in WO 90/13646 published Nov. 15, 1990. In mammalian cell expression the native signal sequence is satisfactory, although other mammalian signal sequences may be suitable, such as signal sequences from other ligand polypeptides or from the same ligand from a different animal species, signal sequences from a ligand, and signal sequences from secreted polypeptides of the same or related species, as well as viral secretory leaders, for example, the herpes simplex gD signal.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in *Bacillus genomic* DNA. Transfection of Bacillus with this vector results in homologous recombination with the genome and insertion of antibody DNA. However, the recovery of genomic DNA encoding antibody is more complex than that of an exogenously replicated vector because restriction enzyme digestion is required to excise the antibody DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al. (1982), J. Molec. Appl. Genet. 1:327) mycophenolic acid (Mulligan et al. (1980), Science 209:1422) or hygromycin (Sugden et al. (1985), Mol. Cell. Biol. 5:410–413). The three examples given above employ bacterial genes under eukaryotic control to convey resistance to the appropriate drug G418 or neomycin (geneticin), xgpt (mycophenolic acid), or hygromycin, respectively.

Examples of other suitable selectable markers for mammalian cells are those that enable the identification of cells competent to take up the antibody nucleic acid, such as dihydrofolate reductase (DHFR) or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes antibody. Amplification is the process by which genes in greater demand for the production of a protein critical for growth are reiterated in tandem within the chromosomes of successive generations of recombinant cells. Increased quantities of antibody are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin (1980), Proc. Natl. Acad. Sci. USA 77:4216. The transformed cells are then exposed to increased levels of Mtx. This leads to the synthesis of multiple copies of the DHFR gene, and, concomitantly, multiple copies of other DNA comprising the expression vectors, such as the DNA encoding antibody-. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding antibody, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al. (1979), Nature 282:39; Kingsman et al. (1979), Gene 7:141; or Tschemper et al. (1980), Gene 10:157). The trp1 gene provides a selection marker for a mutant strain of yeast lacking the ability to grow in tryptophan, for example, ATCC No. 44076 or PEP4-1 (Jones, (1977), Genetics 85:12). The presence of the trp1 lesion in the yeast host cell genome then provides an effective environment-for detecting transformation by growth in the absence of tryptophan. Similarly, Leu2-deficient yeast strains (ATCC No. 20,622 or 38,626) are complemented by known plasmids bearing the Leu2 gene.

(iv) Promoter Component

Expression and cloning vectors usually contain a promoter that is recognized by the host organism and is operably linked to the antibody nucleic acid. Promoters are untranslated sequences located upstream (5') to the start codon of a structural gene (generally within about 100 to 1000 bp) that control the transcription and translation of particular nucleic acid sequence, such as the antibody nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to antibody encoding DNA by removing the promoter from the source DNA by restriction enzyme digestion and inserting the isolated promoter sequence into the vector. Both the native antibody promoter sequence and many heterologous promoters may be used to direct amplification and/or expression of the antibody DNA. However, heterologous promoters are preferred, as they generally permit greater transcription and higher yields of expressed antibody as compared to the native promoter.

Promoters suitable for use with prokaryotic hosts include the β-lactamase and lactose promoter systems (Chang et al. (1978), Nature 275:615; and Goeddel et al. (1979), Nature 281:544), alkaline phosphatase, a tryptophan (trp) promoter system (Goeddel (1980), Nucleic Acids Res. 8:4057 and EP 36,776) and hybrid promoters such as the tac promoter (deBoer et al. (1983), Proc. Natl. Acad. Sci. USA 80:21–25). However, other known bacterial promoters are suitable. Their nucleotide sequences have been published, thereby enabling a skilled worker operably to ligate them to DNA encoding antibody (Siebenlist et al. (1980), Cell 20:269) using linkers or adapters to supply any required restriction sites. Promoters for use in bacterial systems also will contain a Shine-Dalgarno (S.D.) sequence operably linked to the DNA encoding antibody polypeptide.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al. (1980), J. Biol. Chem. 255:2073) or other glycolytic enzymes (Hess et al. (1968), J. Adv. Enzyme Reg. 7:149; and Holland (1978), Biochemistry 17:4900), such as enolase, glyceraldehyde-3-phosphate dehydrogenase, hexokinase, pyruvate decarboxylase, phosphofructokinase, glucose-6-phosphate =isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase., degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Antibody transcription from vectors in mammalian host cells may be controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the antibody sequence, provided such promoters are compatible with the host cell systems.

The early and late promoters of the SV40 virus are conveniently obtained as an SV40 restriction fragment that also contains the SV40 viral origin of replication. Fiers et al. (1978), Nature 273:113; Mulligan and Berg (1980), Science 209:1422–1427; Pavlakis et al. (1981), Proc. Natl. Acad. Sci. USA 78:7398–7402. The immediate early promoter of the human cytomegalovirus is conveniently obtained as a HindIII E restriction fragment. Greenaway et al. (1982), Gene, 18:355–360. A system for expressing DNA in mammalian hosts using the bovine papilloma virus as a vector is disclosed in U.S. Pat. No. 4,419,446. A modification of this system is described in U.S. Pat. No. 4,601,978. See also Gray et al. (1982), Nature 295:503–508 on expressing cDNA encoding immune interferon in monkey cells; Reyes et al. (1982), Nature 297:598–601 on expression of human β-interferon cDNA in mouse cells under the control of a thymidine kinase promoter from herpes simplex virus; Canaani and Berg (1982), Proc. Natl. Acad. Sci. USA 79:5166–5170, on expression of the human interferon S1 gene in cultured mouse and rabbit cells; and Gorman et al. (1982), Proc. Natl. Acad. Sci. USA 79:6777–6781, on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the antibody of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al. (1981), Proc. Natl. Acad. Sci. USA 78:993) and 3' (Lusky et al. (1983), Mol. Cell Bio. 3:1108) to the transcription unit, within an intron (Banerji et al. (1983), Cell 33:729), as well as within the coding sequence itself (Osborne et al. (1984), Mol. Cell Bio. 4:1293). Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv (1982), Nature 297:17–18, on enhancing elements for activation of eukaryotic promoters. The enhancer may be spliced into the vector at a position 5' or 3' to the antibody encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding antibody.

(vii) Construction and Analysis of Vectors Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC No. 31,446) and successful transformants selected by ampicillin or tetracycline resistance where appropriate. Plasmids from the transformants are prepared, analyzed by restriction endonuclease digestion, and/or sequenced by the method of Messing et al. (1981), Nucleic Acids Res. 9:309 or by the method of Maxam et al. (1980), Methods in Enzymology 65:499.

(viii) Transient Expression Vectors

Particularly useful in the practice of this invention are expression vectors that provide for the transient expression in mammalian cells of DNA encoding the antibody polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded-by cloned DNAS, as well as for the rapid screening of such polypeptides for desired biological or physiological properties. Thus, transient expression systems are particularly useful in the invention for purposes of identifying analogues and variants of antibody polypeptide that have antibody polypeptide biological activity.

(ix) Suitable Exemplary Vertebrate Cell Vectors Other methods, vectors, and host cells suitable for adaptation to the synthesis of the antibody in recombinant vertebrate cell culture are described in Gething et al. (1981), Nature 293:620–625; Mantei et al. (1979), Nature 281:40–46; Levinson et al.; EP 117,060; and EP 117,058. A particularly useful plasmid for mammalian cell culture expression is pRK5 (EP 307,247 U.S. Pat. No. 5,258,287) or pSVI6B (PCT Publication No. WO 91/08291).

Suitable host cells for cloning or expressing the vectors herein are the prokaryote, yeast, or higher eukaryotic cells described above. Suitable prokaryotes include eubacteria, such as Gram-negative or Gram-positive organisms, for example, E. coli, Bacilli such as B. subtilis, Pseudomonas species such as P. aeruginosa, Salmonella typhimurium, or Serratia marcescans. One preferred E. coli cloning host is E. coli 294 (ATCC No. 31,446), although other strains such as E. coli B, E. coli X1776 (ATCC No. 31,537), and E. coli W3110 (ATCC No. 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for antibody encoding vectors. Saccharomiyces cerevisiae, or common baker's yeast, is the most commonly used among lower eukaryotic host microorganisms. However, a number of other genera, species, and strains are commonly available and useful herein, such as Schizosaccharomyces pombe (Beach and Nurse (1981), Nature 290:140; EP 139,383 published May 2, 1985), Kluyveromiyces hosts (U.S. Pat. No. 4,943,529) such as, e.g., K. lactis (Louvencourt et al. (1983, J. Bacteriol. 737), K. fragilis, K. bulgaricus, K. thermotolerans, and K. marxianus, yarrowia (EP 402,226), Pichia pastoris (EP 183, 070; Sreekrishna et al. (1988), J. Basic Microbiol. 28:265–278), Candida, Trichoderma reesia (EP 244,234), Neurospora crassa (Case et al. (1979), Proc. Natl. Acad. Sci. USA 76:5259–5263), and filamentous fungi such as, e.g., Neurospora, Penicillium, Tolypocladium (WO 91/00357 published Jan. 10, 1991), and Aspergillus hosts such as A. nidulans (Ballance et al. 1983), Biochem. Biophys. Res. Commun. 112:284–289; Tilburn et al. (1983), Gene 26:205–221; Yelton et al. (1984), Proc. Natl. Acad. Sci. USA 81:1470–1474) and A. niger (Kelly and Hynes (1985), EMBO J. 4:475–479).

Suitable host cells for the expression of glycosylated antibody are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. See, e.g., Luckow et al. (1988), Bio/Technology 6:47–55; Miller et al., Genetic Engineering, Setlow et al. (1986), eds., Vol. 8 (Plenum Publishing), pp. 277–279; and Maeda et al. (1985), Nature 315:592–594. A variety of viral strains for transfection are publicly available, e.g., the L-1 variant of Autographa califdrnica NPV and the Bm-5 strain of Bombyx mori NPV, and such viruses may be used as the virus herein according to the present invention, particularly for transfection of Spodoptera frugiperda cells.

Plant cell cultures of cotton, corn, potato, soybean, petunia, tomato, and tobacco can be utilized as hosts. Typically, plant cells are transfected by incubation with certain strains of the bacterium Agrobacterium tumefaciens, which has been previously manipulated to contain the antibody DNA. During incubation of the plant cell culture with A. tumefaciens, the DNA encoding the antibody is transferred to the plant cell host such that it is transfected, and will, under appropriate conditions, express the antibody DNA. In addition, regulatory and signal sequences compatible with plant cells are available, such as the nopaline synthase promoter and polyadenylation signal sequences. Depicker et al. (1982), J. Mol. Appl. Gen. 1:561. In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

However, interest has been greatest in vertebrate cells, and propagation of vertebrate cells in culture (tissue culture) has become a routine procedure in recent years (Tissue Culture (1973), Academic Press, Kruse and Patterson, editors). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al. (1977), J. Gen Virol. 36:59); baby hamster kidney cells (BHK, ATCC CCL 10); Chinese hamster ovary cells/-DHFR (CHO, Urlaub and Chasin (1980), Proc. Natl. Acad. Sci. USA 77:4216); mouse sertoli cells (TM4, Mather (1980), Biol. Reprod. 23:243–251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al. (1982), Annals N.Y. Acad. Sci. 383:44–68); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with Agrobacterium tumefaciens is used for transformation of certain plant cells, as described by Shaw et al. (1983), Gene 23:315, and WO 89/05859 published Jun. 29, 1989. In addition, plants may be transfected using ultrasound treatment as described in WO 91/00358 published Jan. 10, 1991. For mammalian cells without such cell walls, the calcium phosphate precipitation method of Graham and van der Eb (1978), Virology 52:456–457, is preferred. General aspects of mammalian cell host system transformations have been described by Axel in U.S. Pat. No. 4,399,216 issued Aug. 16, 1983.

Transformations into yeast are typically carried out according to the method of Van Solingen et al. (1977), J. Bact. 130:946, and Hsiao et al. (1979), Proc. Natl. Acad. Sci. (USA)76:3829.

However, other methods for introducing DNA into cells such as by nuclear injection, electroporation, or protoplast fusion may also be used.

Prokaryotic cells used to produce the antibody polypeptide of this invention are cultured in suitable media as described generally in Sambrook et al., supra.

The mammalian host cells used to produce the antibody of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace (1979), Meth. Enz. 58:44, Barnes and Sato (1980), Anal. Biochem. 1.02:255, U.S. Pat. Nos. 4,767,704; 4,657,866; 4,927,762; or 4,560,655; WO 90/03430; WO 87/00195; or U.S. Pat. No. Re. 30,985; the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

Gene amplification and/or expression may be measured in a sample directly, for example, by conventional Southern blotting, northern blotting to quantitate the transcription of MRNA (Thomas (1980), Proc. Natl. Acad. Sci. USA 77:5201–5205), dot blotting (DNA analysis), or in situ hybridization, using an appropriately labeled probe, based on the sequences provided herein. Various labels may be employed, most commonly radioisotopes, particularly $^{32}$p. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al. (1980), Am. J. Clin. Path. 75:734–738.

Antibody preferably is recovered from the culture medium as a secreted polypeptide, although it also may be recovered from host cell lysates when directly expressed without a secretory signal.

When the antibody is expressed in a recombinant cell other than one of human origin, the antibody is completely free of proteins or polypeptides of human origin. However, it is still usually necessary to purify the antibody from other recombinant cell proteins or polypeptides to obtain preparations that are substantially homogeneous as to the ligand per se. As a first step, the culture medium or lysate is centrifuged to remove particulate cell debris. The membrane and soluble protein fractions are then separated. Alternatively, a commercially available protein concentration filter (e.g., AMICON or Millipore PELLICON ultrafiltration units) may be used. The antibody may then be purified from the soluble protein fraction. The antibody thereafter is purified from contaminant soluble proteins and polypeptides by salting out and exchange or chromatographic procedures employing various gel matrices. These matrices include; acrylamide, agarose, dextran, cellulose and others common to protein purification. Exemplary chromatography procedures suitable for protein purification include immunoaffinity, FIX Gla domain affinity (e.g., -IgG or protein A SEPHAROSE), hydrophobic interaction chromatography (HIC) (e.g., ether, butyl, or phenyl Toyopearl), lectin chromatography (e.g., Con A-SEPHAROSE, lentil-lectin-SEPHAROSE), size exclusion (e.g., SEPHADEX G-75), cation- and anion-exchange columns (e.g., DEAE or carboxymethyl- and sulfopropyl-cellulose), and reverse-phase high performance liquid chromatography (RP-HPLC) (see e.g., Urdal et al. (1984), J. Chromatog. 296:171, where two sequential RP-HPLC steps are used to purify recombinant human IL-2). Other purification steps optionally include; ethanol precipitation; ammonium sulfate precipitation; chromatofocusing; preparative SDS-PAGE, and the like.

Antibady variants in wich residues have been delated, inserterd, or substituted are recovered in the same fasion, taking account of any substantial changes in properties occasioned by the variation. For example, preparation of an antibody fussion with another protein or polypeptide, e.g., a bacterial or viral antigen, facilitate purification; an immonoaffinity columm containing antibody to the antigen can be used to absorb the fusion polypeptide. Immunoaffinity columns such as a rabbit polyclonal anti-antibody collumn can be employed to absorb the antibody variant by binding it to at least one remaining immune epitope. Alternatively, the antibady may be purified by affinity chromatography using a purified FIX Gla domain-IgG coupled to a (preferably) immobilized resin such as AFFI-Gel 10 (Bio-Rad, Richmond Calif. or the like, by means well known in the art. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for the native antibady may require, modification to account for charges in the character of the antibody or its variants upon expression in recombinant cell culture.

Utility

The antibodies disclosed herein are useful for in vitro diagnostic assays for inhibiting the activation of FIX to FIXa by FXIa or by TF-FVIIa and in inhibiting coagulation in a FIXa dependent assay.

The compositions of this invention may be used in the treatment and prevention of FIXa mediated diseases or disorders including but are not limited to the prevention of arterial re-thrombosis in combination with thrombolytic therapy. It has been suggested that the FIX plays a significant role in a variety of clinical states including deep venous thrombosis, arterial thrombosis, stroke, DIC, septic shock, cardiopulmonary bypass surgery, adult respiratory distress syndrome, hereditary angioedema as well as tumor growth and metastasis. Inhibitors of FIX may therefore play important roles in the regulation of inflammatory and/or thrombotic disorders.

Thus the present invention encompasses a method for preventing a FIX/FIXa mediated event in a human comprising administering to a patient in need thereof a therapeutically effective amount of the antibody composition of the present invention. A therapeutically effective amount of the antibody molecule of the present invention is predetermined to achieve the desired effect. The amount to be employed therapeutically will vary depending upon therapeutic objectives, the routes of administration and the condition being treated. Accordingly, the dosages to be administered are sufficient to bind to available FIX/FIXa and form an inactive complex leading to decreased coagulation in the subject being treated.

The therapeutic effectiveness is measured by an improvement in one or more symptoms associated with the FIXa dependent coagulation. Such therapeutically effective dosages can be determined by the skilled artisan and will vary depending upon the age condition, sex and condition of the subject being treated. Suitable dosage ranges for systemic administration are typically between about 1 $\mu$g/kg to up to 100 mg/kg or more and depend upon the route of administration. According to the present invention a preferred therapeutic dosage is between about 1 $\mu$g/kg body weight and about 5 mg/kg body weight. For example, suitable regimens include intravenous injection or infusion sufficient to maintain concentration in the blood in the ranges specified for the therapy contemplated.

Pharmaceutical compositions which comprise the antibodies or antibody fragments of the invention may be administered in any suitable manner, including parental, topical, oral, or local (such as aerosol or transdermal) or any combination thereof. Suitable regimens also include an initial administration by intravenous bolus injection followed by repeated doses at one or more intervals.

Where the composition of the invention is being administered in combination with a thrombolytic agent, for example, for the prevention of reformation of an occluding thrombus in the course of thrombolytic therapy, a therapeutically effective dosage of the thrombolytic is between about 80 and 100% of the conventional dosage range. The conventional dosage range of a thrombolytic agent is the daily dosage used in therapy and is readily available to the treating physician. (Physicians Desk Reference (1994), 50th Edition, Edward R. Barnhart, publisher). The typical dosage range will depend upon the thrombolytic being employed and include for tissue plasminogen activator (t-PA), 0.5 to about 5 mg/kg body weight; streptokinase, 140,000 to 2,500,0000 units per patient; urokinase, 500,000 to 6,250,00 units per patient; and anisolated streptokinase plasminogen activator complex (ASPAC), 0.1 to about 10 units/kg body weight.

The term combination as used herein includes a single dosage form containing at least the molecule of the present invention and at least one thrombolytic agent. The term is also meant to include multiple dosage forms wherein the molecule of the present invention is administered separately but concurrently by two separate administration, such as in sequential administration. These combinations and compositions work to dissolve or prevent the formation of an occluding thrombus resulting in dissolution of the occluding thrombus.

When used for in vivo administration, the antibody formulation must be sterile. This is readily accomplished by filtration through sterile filtration membranes, prior to or following lyophilization and reconstitution. The antibody ordinarily will be stored in lyophilized form or in solution.

Therapeutic antibody compositions generally are placed into a container having a sterile access port, for example, an intravenous solution bag or vial having a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

The antibodies of the invention may be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systematically, the therapeutic composition should be sterile, pyrogen-free and in a parenterally acceptable solution having due regard for pH, isotonicity, and stability. These conditions are known to those skilled in the art. Briefly, dosage formulations of the compounds of the present invention are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (e.g., poly(2-hydroxyethyl-methacrylate) as described by Langer et al. (1981), J. Biomed. Mater. Res. 15:167–277, and Langer (1982), Chem. Tech. 12:98–105, or poly(vinylalcohol)), polylactides (U.S. Pat. No. 3,773,919, EP 58,481), copolymers of L-glutamic acid and gamma ethyl-L-glutamate (Sidman et al. (1983), Biopolymers 22:547–556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S-S bond formation through disulfide interchange, stabilization may be achieved by modifying sulfhydryl residues, lyophilizing from acidic solutions, controlling moisture content, using appropriate additives, and developing specific polymer matrix compositions.

The following examples are offered by way of illustration and not by way of limitation. The disclosures of all citations in the specification are expressly incorporated herein by reference.

EXAMPLES

Example I

Reagents. FIX and FXIa was from Haematologic Technologies Inc., (Essex Jct., Vt.). FX was from Enzyme Research Laboratories Inc. (South Bend, Ind.), dioleoyl 1,2-diacyl-sn-glycero-3-(phospho-L-serine) (PS) and oleoyl 1,2-diacyl-sn-glycero-3-phosphocholine (PC) from Avanti Polar Lipids Inc. (Alabaster, Ala.). FIXa chromogenic substrate #299 was from American Diagnostica (Greenwich, Conn.). Actin FS and Innovin were obtained from Dade International Inc. (Miami, Fla.). SEPHAROSE resins and columns were from Amersham Pharmacia Biotech (Piscataway, N.J.). DiaEthyleneglycol (analytical grade) and $FeCl_3$ (reagent grade) were from Mallinckrodt Inc. (Paris, Ky.). Fatty acid-free BSA was from Calbiochem (La Jolla, Calif.). Sodium heparin for injection was from Elkins Sinn Inc. (Cherry Hill, N.J.). Sterile saline for injection was purchased from Baxter Healthcare Corp. (Deerfield, Ill.). Purified TF (1–243) from *E. coli* and recombinant F.VIIa were kindly provided by Robert F. Kelley (Genentech, Inc.).
Methods Synthesis and biotinylation of Gla peptide: Gla peptide synthesis was performed on an ABI431 Peptide Synthesizer using standard Fmoc chemistry protocols on a 0.25 mmol scale. Couplings were carried out with HBTU [2-(1H-benzotriazole-1-yl)-1,1,3,3-tetramethyluronium hexaflourophosphate], HOBT (N-hydroxybenzotriazole), and DIPEA (diisopropylethylamine) for 1 hour. Fmoc amino acid side chain protecting groups were as follows: Tyr(tBut), Thr(tBut), Ser(tBut), Lys(Boc), Arg(pbf), Asn(trt), Gln(trt), Gla(OtBut)2, Cys(acm) and Trp(Boc). Oxidation was carried out with the peptide still on the resin by stirring the resin with 10 equivalents of iodine in DMF at 4° C. for 1 hour. The peptide was cleaved using 70:30:0.1 TFA:dichloromethane-:triisopropylsilane for 3 hours at room temperature, triturated with ether, extracted off the resin with 30 mM NH40H and lyophilized. The identity of the material was confirmed by electrospray mass spectrometry, peptide sequencing and amino acid analysis. Fmoc-L-Gla(OtBut)2 was obtained from Peninsula Labs (Belmont Calif.) and Fmoc-Lys(alloc) from Perspective Biosystems (Framingham Mass.). The catalyst Pd(0) and Biotin-NHS were purchased from Fluka (Ronkonkoma N.Y.) and Sigma (St Louis Mo.), respectively.

Biotinylated Gla peptide synthesis was modified from the above procedure as follows. The peptide synthesis was carried out using Fmoc-Lys(alloc) in position 40 and the final Fmoc group on the N-terminus of the peptide was not removed. Removal of the alloc (allyloxycarbonyl) group was done with a palladium catalyst using a 0.1 M solution of tetrakistriphenylphosphine palladium(0) with 5% acetic acid and 2.5% N-methylmorpholine in chloroform for 3 hours. Biotin-NHS (N-hydroxysuccinimidobiotin) was coupled to the side chain of Lysine(40) with DIPEA overnight in DMF/DCM. Then the final Fmoc group was removed with 20% piperidine/DMF and the peptide was oxidized on the resin, cleaved off the resin and extracted off the resin as described in the previous paragraph.
Results The amino acid sequence of the synthesized Gla peptide is shown in FIG. 1 (human).

Example 2

Methods

Biopanning procedure—A large library of 1010 scFv (Cambridge Antibody Technology, Cambridgeshire, UK) (Vaughan et al. (1996) Nature Biotechnology 14:309–314) was panned through two rounds of enrichment against biotinylated peptide. Affinity-driven selection (Hawkins et al., (1992) J. Mol. Biol. 226:889–896) was performed by decreasing the amount of antigen at each subsequent round of panning (100 nM and 10 nM, for rounds 1 and 2, respectively). To ensure proper conformation of the Gla peptide, calcium chloride (2 mM) was added to all solutions, unless indicated otherwise, during the panning procedure and all subsequent assays. For each selection, approximately $10^{12}$ titered units of phage, blocked in 1 ml of TBS containing 3% skimmed milk, 0.1% TWEEN and 2 mM $CaCl_2$ (MTBST/Ca), were incubated for 1 hr at room temperature (RT) with the biotinylated peptide. Streptavidin-conjugated beads (DYNABEADS, Dynal, Oslo Norway) blocked in MTBS, were added to the phage-biotinylated antigen mixture for 15 min. at RT. A volume of 300 µl of DYNABEADS was used for round 1, and was decreased to 100 µl at round 2. The DYNABEADS were washed three times with each of the following solutions : TBST/Ca, MTBST/Ca, MTBS/Ca, and TBS/Ca, using a Dynal MPC (Magnetic Particle Concentrator). Bound phage were eluted step-wise with 4M $MgCl_2$, 1 mM Tetra-ethylamine (TEA), and 100 mM HCl. Each elution was performed at RT for 5 min, and eluted fractions were neutralized with 50 mM Tris-HCl, pH 7.5. Phage recovered after each round of panning were propagated in the bacterial suppressor strain TG1.
Results Isolation and characterization of scFvs to human FIX—In an attempt to isolate antibodies specific to human FIX with potential anti-thrombotic activity, a phage-displayed library of human scFv antibodies with a peptide corresponding to the Gla domain of human FIX was screened. Since the binding of $Ca^{++}$ to FIX Gla domain was shown to induce conformational changes important for interaction with phospholipids and cell surfaces, all panning selection steps were performed in the presence of 2 mM $CaCl_2$. Two rounds of panning were done in solution with 100 nM and 10 nM of biotinylated peptide, respectively. After the second round of panning, 96 out of 800 clones screened (12%) were selected on their ability to bind to the FIX Gla peptide specifically by phage ELISA (Griffiths et al. (1993), EMBO J. 12:725–734).

Example 3

Methods

Clone characterization—MAXISORP Elisa plates (Nunc) were coated overnight at 4° C. with Gla peptide (5 μg/ml) in HEPES buffered saline (HBS). Plates were blocked with HBS buffer containing 0.1% TWEEN and 3% milk powder. Phage culture supernatants (50 μl) were directly applied to the plates. Horseradish peroxidase (HRP)-conjugated anti-M13 (Pharmacia, Uppsala, Sweden) was then added. DNA purified from selected clones was characterized by BstNI digestion and sequencing (ABI377, Perkin Elmer, Foster City, Calif.).

ScFv protein ELISA—ELISA plates were coated with either the anti-c myc antibody 9E10 in carbonate buffer (format I), FIX or FIX-related factors, in HBS with 2 mM $CaCl_2$ (HBSCa) (format II). Plates were blocked with HBSCa containing 0.1% TWEEN (HBST/Ca). ScFv were added at a concentration of 5 μg/ml. In format I, biotinylated FIX (1ug) was applied to the plates followed by Streptavidin-HRP. In format II, detection of scFv was performed using 9E10 anti-c myc mAb and an HRP-conjugated goat anti-mouse Fc-specific mAb (Zymed, South San Francisco, Calif.). All reagent dilutions were prepared in blocking buffer HBST/Ca and plates were washed with HBS/Ca containing 0.05% Tween.

Results

To further assess germline diversity of the selected clones, DNA was purified from individual clones and subjected to BstNI fingerprinting (Clackson et al, (1991) Nature 352:624–628). The 96 clones were classified into 24 distinct fingerprint families. ScFvs were expressed as epitope-tagged proteins containing a c-myc tag sequence recognized by monoclonal antibody 9E10 (Griffiths et al. (1993), EMBO J. 12:725–734) and a polyhistidine tag (his6) and were purified over Ni-NTA with imidazole elution as recommended by the manufacturer (Qiagen, Chatsworth, Calif.). One clone from each fingerprint family was selected for scFv expression. Purified scFv were then tested for their reactivity to Gla peptide and full length FIX by ELISA. Out of the 24 clones tested, six clones (10C12, 11C5, 11G9, 13D1, 13H6, and 14H9) were shown to crossreact to various extent with both the Gla peptide and full length FIX by ELISA (FIG. 4); all others reacted with Gla peptide only. Clones 10C12, 13D1 and 13H6 exhibited stronger binding to FIX than clones 11G9, 11C5, and 14H9.

These six clones were further characterized by DNA sequencing to analyze segment usage (FIG. 2). Four clones (10C12, 11C5, 11G9, and 13D1) displayed the same light chain (Vλ1) with identical CDR regions. Clones 13H6 and 14H9 light chains were unique and different from the others, with no homology found in the CDR regions. Sequencing of the heavy chains revealed strong homology between clones 10C12 and 13D1 with differences at only 3 residues, one located in $CDR_2$ and two in the frame work regions. Clone 11C5 heavy chain had almost identical CDR1 and CDR2 as 10C12 and 13D1 but a different $CDR_3$ region. Clones 13H6 and 14H9 heavy chains showed little homology to the other clones. These results show that 10C12, 11C5, 11G9, and 13D1 are closely related, the most striking difference residing in clone 11C5 heavy chain $CDR_3$ region. The overall homology suggests that these antibodies bind an identical epitope within the FIX-Gla domain. In the presence of Ca++ and Mg++, the FIX Gla domain adopts different conformations which expose distinct antibody epitopes. The antibodies 10C12, 13D1, 11C5 and 13H6 which display high homology in their CDRs (except for 13H6) exclusively bound to the Ca++ induced conformation of the Gla domain, consistent with the view that they recognize a common epitope. In contrast, clones 13H6 and 14H9 both have unique heavy and light chains. Clone 14H9 appears to have significantly more charged residues in the CDR domains, especially in $CDR_3$.

Four of the six antibodies were chosen to be reformatted as $F(ab')_2$ molecules, based on strong FIXa inhibiting activity (10C12, 13D1, and 13H6) and DNA germline diversity (14H9).

Binding specificity of scFvs and $F(ab')_2$ to various blood coagulation factors—There is a high degree of homology between Gla domains of different blood coagulation factors (FVII, FIX, FX, prothrombin, and protein C) (see FIG. 1B). To determine the specificity of the antibodies selected for binding to FIX Gla domain, ELISA experiments were performed by coating various factors (FIX, FVII, FX, prothrombin and protein C) onto plates and incubating with scFvs (FIG. 6A) or $F(ab')_2$ (FIG. 6B) at a concentration of 5 μg/ml (0.02 μg/ml for $F(ab')_2$). Results showed that both scFv and $F(ab')_2$ from clones 10C12, 13D1 and 13H6 reacted with FIX only while 14H9 recognized all factors tested. Moreover, binding of scFv from clones 10C12, 13D1 and 13H6 to FIX was not reduced when scFvs were preincubated with FIX deficient serum, ruling out any interaction of these clones with factors, other than FIX, present in the serum. In contrast, binding of scFv from clone 14H9 was greatly diminished after incubation of scFv with the same serum. These results demonstrated that the epitope recognized by clone 14H9 is unique and different from the sequence seen by the other 3 antibodies.

Calcium and magnesium dependence of anti-FIX $F(ab')_2$ binding to FIX—The selection of scFv antibodies described in this study was performed in presence of $Ca^{++}$ ions. FIX has been shown to undergo two metal-dependent conformational transitions, one metal-dependent but cation non-selective, the second one metal-selective for $Ca^{++}$ or $Sr^{++}$. To test the influence of metal ions on the binding of the anti-FIX antibodies, ELISA experiments were performed with either $Ca^{++}$, $Mg^{++}$, or EDTA (which chelates $Ca^{++}$ ions) added to all buffers. Results indicated that clones 10C12, 13D1 and 13H6 recognized FIX only in the presence of Ca++, and the binding was partially or completely inhibited in presence of 2 mM EDTA. In contrast, clone 14H9 did bind to FIX in presence of either $Mg^{++}$ or $Ca^{++}$. No inhibition was observed in presence of EDTA which demonstrated that $Ca^{++}$ ions were not necessary for the binding to occur.

Example 4

Methods

BIAcore evaluation of anti-FIX $F(ab')_2$ affinities—The antigen-binding affinities of several $(Fab')_2$ "leucine-zipper" fragments were calculated (Löfas & Johnsson (1990), J. Chem. Soc. Commun. 21:1526–1528) from association and dissociation rate constants measured using a BIAcore-2000™ surface plasmon resonance system (Pharmacia Biosensor). A biosensor chip was activated using N-ethyl-N'-(3-dimethylaminopropyl)-carbodiimide hydrochloride (EDC) and N-hydroxysuccinimide (NHS) according to the supplier's (BIAcore, Inc., Piscataway, N.J.) instructions. Factor IX, and Factor X as a negative control, were diluted approximately 30 μg/mL in 10 mM sodium acetate buffer (pH 4.5). Aliquots were injected to achieve approximately 519 response units (RU) of coupled FIX, and 2330 RU or 13,590 RU of coupled FX. Finally, 1M ethanolamine was injected as a blocking agent.

For kinetics measurements, 2-fold serial dilutions (10 μL) of antibody were injected in running buffer (0.05% Tween-20, 150 mM NaCl, 2 mM $CaCl_2$, 10 mM Hepes pH 7.4) at 25° C. using a flow rate of 10 μL/min. Regeneration was achieved with 4.5 M $MgCl_2$, followed by wash solution (50 mM EDTA, 150 mM NaCl, 0.05% TWEEN-20). Equilibrium dissociation constants, Kd's, from SPR measurements were calculated as $k_{off}/k_{on}$. Dissociation data were fit to a simple 1:1 Langmuir binding model. Pseudo-first order rate constant (ks) were calculated for each association curve, and plotted as a function of protein concentration to obtain $k_{on}$ +/− s.e. (standard error of fit). The resulting errors e[K] in calculated $K_d$'s were calculated as follows:

$$e[K]=[(k_{on})^{-2}(S_{off})^2+(k_{off})^2(k_{on})^{-4}(S_{on})^2]^{1/2}$$

where $s_{off}$ and $s_{on}$ are the standard errors in $k_o$ and $k_{off}$, respectively.

Results

Affinity measurement of anti-FIX $F(ab')_2$ binding to FIX-In SPR binding experiments, $F(ab')_2$-zipper forms of 10C12, 13D1, and 13H6 showed specific binding to FIX (versus F.X, or a blank flow cell). For these experiments, a low density (519 RU) of immobilized antigen (FIX) was used. Although the bivalent form of the antibodies could have resulted in avidity effects in binding to antigen, the binding kinetics observed were consistent with simple 1:1 models of association and dissociation. All three antibodies had similar dissociation rate constants ($k_{off}$), corresponding to dissociation half-lives of about 50–70 minutes (FIG. 3). The association rate ($k_{on}$) for 13H6, however, was significantly faster than 10C12 or 13D1. Consequently the equilibrium dissociation constant ($K_d$) for 13H6 is lower ($Kd_d$=0.45 nM) than 10C12 ($K_d$=1.6 nM) or 13D1 (2.9 rM)

Example 5

Methods

FIX binding to bovine endothelial cells—Primary bovine aortic endothelial cells were grown as described (Marcum et al. (1986), J. Biol. Chem. 261:7507) for four days. Cells were washed with Hepes buffer containing 10 mM HEPES pH 7.2, 137 mM NaCl, 4 mM KCl, 11 mM Glucose, 5 mg/ml BSA and 2 mM $CaCl_2$. Cells were then incubated at 4° C. for 2 hours with biotinylated FIX, and/or biotinylated FIX preincubated for 1 hour with various amounts of cold FIX, scFv or $F(ab')_2$ proteins. Plates were washed and a Streptavidin-HRP conjugate was added for 1 hour at RT, followed by $TMB/H_2O_2$ substrate. Plates were analyzed on a plate reader at 620 rm.

Platelet-dependent coagulation assay—Microtiter plates (Linbro # 76-232-405) were coated with 4 μg/ml of human collagen III (GibcoBRL #12167-011) in PBS, 11 mM $CaCl_2$, 1 mM Mg $Cl_2$ overnight at 4° C. After washing with PBS the plates were further incubated with Tyrode's BSA, 2 mM $CaCl_2$ for 60 min. at 37° C. before use.

Washed platelets were prepared from human citrated whole blood as described (Dennis et al. (1989), Proc. Natl. Acad. Sci. USA 87:2471–2475). The washed platelets were adjusted to a concentration of approximately $6\times10^8$ platelets/ml in Tyrode's BSA and allowed to rest for 120 min. at 37° C. After adding 1 mM $CaCl_2$ and 1 mM $MgCl_2$, the platelets were activated with ADP (10 μM final conc.). 60 μl of platelet suspension was added per well, the plate centrifuged at 60 xg for 5 min. and then the platelets were allowed to firmly adhere to the collagen-coated wells for 60 min at room temperature. The nonadherent platelets were gently decanted and the plate washed twice with PBS containing 1 mM $CaCl_2$ and 1 mM Mg $Cl_2$. The collagen-adherent platelet layer was then incubated for 10 min with the antibodies in Tyrode's BSA-2 mM $CaCl_2$ (40 μl/well). 60 Al of human citrated plasma (plasma pool from Peninsula Blood Bank) recalcified with $CaCl_2$ (to 11 mM final conc.) was added to each well. Coagulation was quantified by monitoring the increase in optical density at 405 nm on a kinetic microplate reader (SLT Lab Instruments, model EAR 340AT).

Results

Potent inhibitory effect of scFvs on FIX binding to endothelial cells and on platelet-dependent coagulation—Since the Gla domain of FIX is known to be required for the interaction of FIX with phospholipid and cell surfaces (Ryan et al. (1989), J. Biol. Chem. 264:20283–20287; Toomey et al. (1992), Biochemistry 31:1806–1808; Cheung et al. (1992), J. Biol. Chem. 267:20529–20531; Ahmad et al. (1994), Biochem. 33:12048–12055), scFv generated against FIX Gla domain were further tested for their ability to block the binding of FIX to endothelial cells. In a competition assay using bovine aortic endothelial cells, binding of biotinylated FIX to the cells was measured in absence or presence of scFvs from either clones 10C12, 11C5, 11G9, 13D1, 13H6, 14H9, 6E11 or unlabeled FIX. The results of this experiment are shown in FIG. 5A. ScFv from clones 10C12, 13D1, 13H6 and 11G9 exhibited the most potent inhibitory effect on FIX binding, similar to unlabeled FIX (IC50 equivalent to 20–50 nM). ScFv from clones 11C5, 6E11 and 14H9 showed much weaker inhibition (IC50>300 nM).

The FIX Gla domain also contains a major determinant for binding to platelets (Ahmad et al. (1994), supra). A human platelet-dependent plasma coagulation assay was used to assess the potency of the various scFvs as inhibitors of FIX activity. In this assay, washed human platelets were activated and allowed to adhere to collagen, and platelet-free recalcified human plasma was added. The ongoing coagulation was monitored as change in optical density up to 90 min. Omission of the platelets or use of FIX-deficient plasma in the presence of platelets did not lead to any significant change in absorbance over this time period. These findings indicate that coagulation in this in vitro system is dependent on platelets and FIXa activity. As shown in Figure 5B, scFv from clones 10C12, 11G9, 13H6, and 13D1 completely inhibited clot formation at a concentration of 500 nM. At this concentration, 14H9 had no effect whereas 11C5 showed an intermediate response. At a higher concentration (2 μM), both of these scFv were completely inhibitory. The potencies of the examined scFvs to interfere with FIXa function in this system rank in the same order as in the endothelial cell binding assay. This may indicate that similar structural elements of the Gla domain are recognized by endothelial cells and platelets.

Example 6

Methods

Plasma clotting assays—The activated partial thromboplastin time (APTT) and prothrombin time (PT) of plasma from different species were measured on a ACL 300 (Coulter Corp., Miami, Fla.) using Actin FS (Dade Diagnostics, PR) and human relipidated tissue factor reagent Innovin (Dade International Inc., Miami, Fla.) as coagulation initiators. For the rabbit PT, rabbit thromboplastin C Plus (Dade Diagnostics, PR) was used. Innovin was a potent initiator of clotting across all species examined here, in agreement with the findings of Janson et al. (1984) Haemostasis 14:440–444 that human relipidated tissue factor can effectively clot plasma from different animal species. The plasma derived from citrated blood of New Zealand white rabbits, C-57 mice, Sprague-Dawley rats and dogs were prepared by standard procedures and stored at −80° C. Human pooled plasma was obtained from the Peninsula Blood Bank (Burlingame, Calif.). The anti-FIX antibodies were incubated diluted 10-fold in citrated plasma and incubated for 10 min before clotting was started by adding Actin FS and $CaCl_2$ (for APTT) or Innovin (for PT). The effect of the antibodies was expressed as x-fold prolongation which is the ratio of clotting times in the presence and absence (=control) of antibody.

FX activation by the FVIIIa:FIXa complex on phospholipids —A mixture of 0.5 nM Factor IXa, 0.7 U/ml F.VIII, 200 μM phospholipid vesicles (PC:PS=7:3) and 10 mM $CaCl_2$ in HBSA buffer (0.1 M Hepes, pH 7.5, 0.14 M NaCl, 0.5 mg/ml fatty acid-free BSA) was incubated with α-thrombin (2.8 nM) for 1 min at room temperature to activate FVIII. Thrombin activity was neutralized by addition of 23.3 nM hirudin. The antibodies were added to the mixture and incubated for 20 min at RT before 0.8 μM FX was added. In this final reaction mixture the concentration of reactants was: 0.25 nM FIXa, 0.35 U/ml F.VIIIa, 25 μM phospholipids, 100 nM FX and 5 mM $CaCl_2$. At different time points 50 μl aliquots were added to 150 μl of 20 mM EDTA to stop the reaction. To measure the FXa concentration in the samples, 50 μl of 1.5 mM S-2765 was added to each well and the change in absorbance monitored on a kinetic microplate reader (Molecular Devices, Menlo Park, Calif.). The rates of FXa generation were determined by using linear regression analysis of the FXa concentrations vs. time.

Results

Selective inhibition of FIX function by 10C12 and 13H6 F(ab')$_2$—A number of different functional assays were employed to investigate whether the observed specific binding to FIX by 10C12 and 13H6 also translated into a specific inhibition of FIX/IXa function. Both 13D1, due to its identity to 10C12, and 14H9, due to its non-specific binding pattern, were not pursued further. Firstly, we measured the effects of 10C12 and 13H6 on the FIX-dependent APTT and the FIX-independent PT in human plasma. As shown in FIG. 9A, both antibodies specifically prolonged the APTT but did not change the PT. A control F(ab')$_2$ (anti-neurturin) neither prolonged the APTT nor the PT. Secondly, both 10C12 and 13H6 F(ab')$_2$ strongly interfered with platelet-dependent coagulation, similar to the results obtained with their single chain forms. 10C12 was more potent than 13H6 with an $IC_{50}$ of 59.0±3 nM compared with 173±43 nM (FIG. 7).

Cross-species reactivity of 10C12 F(ab')$_2$—The amino acid sequences of FIX-Gla domains of different animal species are much conserved (FIG. 1A), suggesting that an antibody that binds to human FIX-Gla may also recognize plasma FIX/IXa of various animals. The potency of 10C12 F(ab')$_2$ to inhibit the APTT in plasma from different species was therefore examined. As shown in FIG. 9B, 10C12 F(ab')$_2$ most potently prolonged the APTT in dog and to a lesser extent than in rat and rabbit plasma. The specificity of the antibody effect towards FIX/IXa was evidenced by the absence of any effect on the PT in homologous plasma.

The antibodies were evaluated in a FVIIIa:FIXa-mediated FX activation assay using phospholipid vesicles (PCPS) (FIG. 8). A concentration-dependent inhibition of FX activation rates was observed with half-maximal rate inhibitions of 3.5±1.8 nM for 10C12 and 7.3±1.3 nM for 13H6. A non-relevant control F(ab')$_2$ directed against neurturin (α-NTN) did not affect the activation rate. Moreover, the antibodies had no effect on the FXa activity to cleave chromogenic substrate S2765 which was used in the second stage of the assay to determine the concentration of newly formed FXa. Therefore, the effect of the antibodies was solely due to interference with intrinsic Xase function. Together these results indicated that both 10C12 and 13H6 F(ab')$_2$ specifically inhibited FIX/FIXa function in agreement with their demonstrated binding specificity in ELISA-type assays.

Example 7

Inhibitory Mechanism of 10C12

Methods

Activation of FIX by FXIa. Antibodies were incubated with FIX in 20 mM hepes, pH7.5, 0.15M NaCl, 5 mM $CaCl_{21}$ 0.05% BSA (HBSA buffer) using microtiter tubes (8.8×45 mm, OPS, Petaluma, Calif.). After a 20 minute incubation period FXIa was added to start the reaction. The concentration of FIX and FXIa in this reaction mixture were 400 nM and 1 nM, respectively. 100 μl aliquots were taken at 30 sec intervals and quenched in 96-well Costar plates (Corning Inc., Corning, N.Y.) containing 125 μl of 30 mM EDTA buffer-60% (v/v) ethyleneglycol. Ethyleneglycol was included because of its enhancing effect on FIXa amdiolytic activity (Sturzebecher et al., (1997) FEBS lett., 412:295–300; Neuenschwander et al., (1997) Thromb. Haemostatsis 78 (Suppl.):428). After adding 25 μl of 5 mM FIX substrate #299, FIXa amidolytic activity was measured at 405nm on a kinetic microplate reader (Molecular Devices, Menlo Park, Calif. Inhibition by the tested antibodies was expressed as fractional rates (vi/vo) of FIXa generation.

Activation of FIX by tissue factor:F.VIIa complex. TF(1-243) lacking the cytoplasmic domain (Paborsky et al. (1989), Biochemistry 28:8072; Paborsky et al. (1991), J. Biol. Chem. 266:21911–21916) was relipidated with PC/PS (7:3 molar ratio) according to Mimms et al. (1981), Biochemistry 20:833–840. Membrane TF (mTF) was prepared from a human embryonic kidney cell line (293) expressing full length TF (1–263) (Kelley et al. (1997), supra). The cells were washed in PBS, detached with 10 mM EDTA and centrifuged twice (2500 rpm for 10 min). The cell pellet (4–5×107 cells/ml) was resuspended in Tris, pH 7.5 and homogenized in PBS using a pestle homogenizer, followed by centrifugation (2500 rpm on a Beckman GSA) for 40 min at 4° C. The protein concentration of the cell membrane fraction was determined and the membranes stored in aliquots at −80° C. until use.

Antibodies were incubated with FIX in HBSA buffer for 20 min in microtiter tubes. A complex of relipidated TF (1–243) (20 nM) and FVIIa (5 nM) was pre-formed for at least 10 min before it was added to the FIX/antibody incubation solution. In this reaction mixture the concentrations of relipidated TF (1–243), FVIIa and FIX were 4 nM, 1 nM and 400 nM, respectively. For experiments with mTF, a complex of mTF (membrane protein conc of 750 μg/ml) and 5 nM FVIIa was pre-formed. This concentration of mTF gave maximal FVIIa activity and was equal to that seen with relipidated TF (1–243). The concentration of mTF and FVIIa in the reaction mixture was 150 μg/ml (membrane protein concentration) and lnM, respectively. 100 μl aliquots of the reaction mixture were taken at 30 sec intervals and quenched in 96-well plates (Costar) containing 125 μl of 30 mM EDTA-buffer-60% (v/v) ethyleneglycol. After adding 25 µl of 5 mM FIX substrate #299, FIXa amidolytic activity was measured at 405 nm on a kinetic microplate reader (Molecular Devices, Menlo Park, Calif. Inhibition by the tested antibodies was expressed as fractional rates (vi/vo) of FIXa generation. Using standard curves with FIXab, it was determined that, in both the TF:FVIIa and the FXIa assay, less than 15% of zymogen FIX was converted during the reaction period.

Results

Inhibitory mechanism of 10C12.

The effects of 10C12 on FIX activation mediated by FXIa and the TF:FVIIa complex were examined. Recently, Stuerzebecher et al. (1997), Febs lett. 412:295–300, and Neuenschwander-et al. (1997), Thromb. Haemostasis 78(suppl.):428 reported that ethyleneglycol enhanced FIXa amidolytic activity towards certain types of chromogenic substrates. A FIX activation assay using ethylenglycol to increase the amidolytic activity of newly generated FIXa was derived. As shown in FIG. 10A, 10C12 inhibited conversion of FIX into FIXa by FXIa in a concentration-dependent manner ($IC_{50}$ 28.8±1.7 µg/ml; ±SD). A control antibody, anti-neurturin (NTN), which was also formatted as a leucine-zippered F(ab')$_2$, had no effect. Because 10C12 binds to the Gla domain of FIX and FIXa, it was not expected that 10C12 would interfere with the ability of FIXa to cleave small chromogenic substrate used to measure the concentration of generated FIXa in the assay. To confirm this assumption, increasing concentrations of FIXa were incubated with 100 µg/ml of 10C12 and assayed with FIXa substrate. 10C12 did not change the rates of substrate cleavage by FIXa, indicating that 10C12 solely inhibited FXIa-dependent activation of FIX, and not FIXa amidolytic activity.

Furthermore, the effects of 10C12 on the extrinsic activation of FIX were measured by using a complex of relipidated TF(1–243) and FVIIa. 10C12 inhibited conversion of FIX with a half-maximal inhibition at 34.2±1.6 µg/ml, while a control antibody (NTN) had no effect (FIG. 10B). Then, membrane TF (mTF) was used instead of relipidated TF(1–243). As for the assays with relipidated TF(1–243), the concentration of mTF used were saturating in respect to FVIIa enzymatic activity. The results showed that inhibition of FIX activation by 10C12 was inhibited in a similar fashion with an $IC_{50}$ at a somewhat lower concentration (15.4±0.7 µg/ml; ±SD) as compared to relipidated TF(1–243) (FIG. 10B). To further evaluate the specificity of 10C12 for FIX, interference with the function of two other Gla-containing coagulation factors, FVIIa and FX was examined. The rates of FX (200 nM) activation by the relipidated TF(1–243):FVIIa (0.2 nM/0.04 nM) complex were measured either after incubating 10C12 for 20min with FVIIa or with the substrate FX. 10C12 at up to 200 µg/ml did not inhibit FXa generation in either experimental setting, confirming the specificity of the 10C12 antibody.

Specific inhibition of FIX-dependent coagulation in guinea pig/rat plasma. Whether the specific inhibition of human FIX function by 10C12 was maintained for guinea pig and rat FIX was examined. 10C12 was incubated with platelet-poor plasma derived from citrated blood of rat and guinea pig, and the effects on APTT and PT were measured. 10C12 specifically prolonged the APTT in both guinea pig and rat plasma (FIG. 11). Two-fold APTT prolongation was at 65 µg/ml (650 nM) and at 60 µg/ml (600 nM) for guinea pig and rat, respectively. These potencies were almost identical to that in human plasma where 10C12 gave a 2-fold APTT prolongation at 60 µg/ml. A control antibody (NTN) neither affected the APTT nor the PT. These data suggested that 10C12 bound and neutralized FIX/IXa in plasma of guinea pig and rat, yet maintained its specificity, as indicated by the unchanged PT. The observed cross-species reactivity and specificity of 10C12 allowed us to examine the anti-thrombotic activity in established thrombosis models in guinea pig and rat.

Example 8

Administration of Anti-IX/IXa Gla Domain Antibodies Prevents Cyclic Flow Variations in Damaged Carotid Arteries Without Affecting Coagulation or Bleeding Parameters Methods Production and purification of leucine-zippered 10C12 F(ab')$_2$ antibody. cDNAs encoding the variable heavy and light chain of clone 10C12 were amplified by PCR and subcloned into an expression vector containing both human heavy ($F_d$) and light chain (lambda) constant regions (Carter et al. (1992) Bio/Technology 10:163–167) as well as a leucine zipper sequence (Kostelny et al. (1992), J. Immunol. 148:1547–1553) added at the 3' end of the constant heavy chain sequence. This vector was expressed in E. coli K12 strain 33B6 (fhuAphoA-delta-E15delta(argF-lac)169 deoC2 degP41(deltaPstI-kanR) IN(rrnDrrnE)1 ilvG2096), derived from the strain W3110. Cells were grown for 46 hours in an aerated 60 liter fermentor at 30° C. in a medium that initially contained 12 mg/l tetracycline, 12 g/l digested casein, 5 mM glucose, 47 mM $(NH4)_2SO_4$, 10 mM $NaH_2PO_4$, 18 mM $K_2HPO_4$, 4 mM trisodium citrate, 12 mM $MgSO_4$, 250 mM FeCl3, and 40 mM each of $ZnSO_4$, $MnSO_2$, $CuSO_4$, $CoCl_2$, $H_3BO_3$, and $NaMoO_4$. The fermentation received an automated feed of ammonia:leucine (35:1 molar ratio) to maintain the pH at 7.0 and glucose, adjusted to the highest rate that would prevent acetate accumulation. Operating conditions were sufficient to supply oxygen at 3 mmol/l-min. Expression was induced by phosphate starvation. Final cell density was 160 $OD_{550}$. Harvested E. coli cell pellet was stored frozen at −70° C. The frozen pellet was broken into small pieces with a mallet and mixed with 5 volumes of 20 mM MES (2-{N-Morpholino} ethane-sulfonic acid)/2 M urea/5 M EDTA/0.25 M NaCl, pH 5.0 (extraction buffer) using an ulturaturax tissue homogenizer until a uniform suspension was achieved. The cell suspension was then passed through a homogenizer (Model 15M, Gaulin Corp., Everett, Mass.) to disrupt the cells. The extract was clarified by adjusting the mixture to pH 3.5 with 6 N HCl and centrifuging for 20 minutes at 6000×g. The pH of the supernatant was readjusted to 5.0 using NaOH. The supernatant was conditioned for chromatography by dilution with 4 parts 20 mM MES/2 M urea, pH 5.0, filtered through a 0.2 micron filter (Millipore Corp., Bedford, Mass.) and applied to a SP-SEPHAROSE fast flow cation exchange resin equilibrated in the dilution buffer. The column was washed extensively in the same buffer and then with 20 mM MES, pH 5.0. The column was eluted in two steps using 0.5 M NaCl and 1 mM NaCl in 20 m MES buffer, pH 5.0. The 10C12 leucine-zippered F(ab')$_2$ was recovered in the 1 mM NaCl/20 nM MES fraction. The SP-SEPHAROSE pool was loaded in multiple cycles to a Protein G-SEPHAROSE fast flow column. The column was equilibrated and washed with 20 mM Tris/0.5 M NaCl, pH 7.5. Elution was with 0.1 M acetic acid/0.15 M NaCl, pH 3.0, and the column was regenerated after each cycle with 20 mM Tris/2 M guanidine HCl, pH 7.5. The combined protein G pools were concentrated approximately 20-fold using an Amicon stirred cell system (Amicon Inc., Beverly, Mass.) equipped with a YM30 membrane. The concentrated pool was buffer exchanged using a SEPHADEX G25 column run in 20 m $NaPO_4$/0.15 mM NaCl, pH 7.0. The G25 pool was passed through a Q-SEPHAROSE fast flow column in 20 mM $NaPO_4$/0.15M NaCl, pH 7.0, for endotoxin removal. The final pool contained 12.5 EU/mg protein and was passed through a 0.22 micron filter.

As a control antibody for all experiments, the anti-neurturin leucine-zippered F(ab')$_2$ antibody (NTN) was used. This antibody was also produced in *E.coli* and was purified over a protein G fast flow column. The leucine-zippered control F(ab')$_2$ and the leucine-zippered 10C12 F(ab')$_2$ will be simply referred to as anti-neurturin antibody (NTN) and 10C12 antibody. The molecular weight of both antibodies was calculated as 100,000.

Arterial thrombosis model in the guinea pig. Experiments were performed as described by Carteaux et al. (1995), Circulation 91:1568–1574). GOHI male guinea pigs (350–450 g, BRL, Füllinsdorf, Switzerland) were anesthetized by i. m. injection of 40 mg/kg ketamine HCl (Ketasol-100$^R$, Gräub AG, Bern, Switzerland) and 5 mg/kg xylazine 2% (Rompun$^R$, Bayer AG, Leverkusen, Germany). A catheter pressure transducer (Millar 2F Mikro-Tip SPC-320 Millar Instr. Inc. Houston, Tex.) was inserted into the right femoral artery to measure blood pressure and heart rate. Into the left femoral artery was placed a catheter (TriCath In 22G, Codan, Espergaerde,DK) for blood sampling. A left jugular vein catheter (TriCath In 22G) was also inserted for drug administration. The right carotid artery was dissected free and a 0.8 mm diameter silicone cuff-type Doppler flow probe (type D-20-0.8, Iowa Doppler Products, IA) was connected to a 20 MHz pulsed Doppler flowmeter module (System 6-Model 202, Triton Technology, Inc. San Diego, Calif. to monitor the blood flow velocity. Blood pressure (mm Hg), heart rate (beats/min) and carotid blood flow velocity (Volts) were recorded on a Graphtec Linear recorder VII (Model WR 3101, Hugo Sachs, March-Hugstetten, Germany).

Guinea pigs received a single bolus of saline, 10C12 or control antibody (NTN) via the left jugular vein catheter and after 15 minutes vascular damage was initiated. Two millimeter distally to the Doppler flow probe, damage to the subendothelium was induced by pinching a 1-mm segment of the dissected carotid artery with a rubber covered forceps during 10 s as previously described (Carteaux et al. (1995), supra; Roux et al. (1994), Haemostasis 71:252–256). After damage, the carotid blood flow velocity would typically decline to complete occlusion followed by restoration of flow upon gentle shaking of the damaged area to dislodge the thrombus. The pattern of cyclic flow variations (CFVs) were established similar to those described by Folts (1991), Circulation 83:Supple. IV:3–14) in a dog coronary thrombosis model. If no CFVs were observed for 5 minutes, an additional pinch was performed on top of the first damage. The same procedure was repeated every 5 minutes till CFVs occurred. Finally, the number of pinches necessary to produce the CFVs were counted over the 40-minute observation period. It was assumed that several pinches are likely to increase the thrombogenicity of the subendothelial layer of the carotid artery, thus a thrombosis index was calculated as the ratio of the number of CFVs to the number of pinches (Carteaux et al. (1995), supra). Under these experimental conditions the calculated shear rate of the carotid artery was around 1500–2800 s$^{-1}$ (Roux et al. (1994), supra).

Blood was collected prior to inhibitor administration (pre-value) and at 60 min following drug administration (post-value) for measurement of activated clotting time (ACT), prothrombin time (PT), activated partial thromboplastin time (APTT) and blood cell counts. Nail cuticle bleeding times were also measured in these animals at the pre- and post-experimental periods. Thrombus initiation and sample collection times were based on a pilot pharmacokinetic study in which prolongation of APTT reached a maxima within 15 minutes of IV bolus dosing (5 mg/kg, n=2) and then remained essentially unchanged over the following 2 hours. Sample handling, coagulation assays and bleeding time methods are described below.

Cuticle bleeding time measurements in the guinea pig. The cuticle bleeding method was adapted from dog (Giles et al. (1982), Blood 60:727–731) and rabbit (Kelley et al. (1997), Blood 89:3219–3227, Himber et al. (1997), Haemostasis 78:1142–1149) models of coagulation dependent bleeding. A standard cut was made at the apex of the nail cuticle by the mean of scissors. Blood was allowed to flow freely by maintaining the paw in contact with the surface of 38° C. water. Cuticle bleeding time was determined as the amount of time that blood continued to flow from the transected cuticle. This procedure was performed in triplicate for both pre- and post-dose (60 minutes) determinations. The ratio of post-treatment to pre-treatment was calculated by dividing the mean of the post-treatment value by the mean of the pre-treatment value.

Results

Antithrombotic and hemostatic effects of 10C12 in guinea pig. To evaluate 10C12's antithrombotic potential in-vivo, a previously established guinea pig arterial thrombosis model of cyclic flow variations (CFVs) was used. In 12 control animals which received saline, the number of CFVs during the 40min measurement period was 11.2±1 (±SEM) and the calculated thrombosis index was 9.3±1.5. Administration of a control antibody (NTN) gave 13.7±1.8 CFVs and a thrombosis index of 12.5±2.11. Neither of these thrombotic nor any of the hemostatic endpoints were significantly different from the saline control. Therefore, saline and NTN control data were pooled for subsequent comparison to 10C12 treatments. The mean(±SEM) thrombosis index of the pooled controls was 10.4±1.2. As shown in FIG. 12, bolus administration of increasing concentrations of 10C12 resulted in a dose-dependent reduction of CFVS, reaching a highly significant reduction at 6 μg/kg (p<0.01) and complete inhibition of CFVs at 60 μg/kg. At all tested doses, including 1000 μg/kg, the blood pressure, heart rate, hematocrit, and blood cell counts remained unchanged (data not shown). Likewise, 10C12 did not significantly affect (p>0.05 in Kruskal-Wallis test) the APTT, ACT or PT up to 1000 μg/kg (Table I). However there was a dose dependent increase in APTT and ACT but not PT which reached statistical significance (p≤0.01) at 1000 μg/kg if a 2-tail t-test was used to compare individual dose groups against the control.

TABLE I

Effects of 10C12 antibody on coagulation parameters in guinea pig. Data are mean ± SEM

| Rx | Number of animals | APTT prolongation (post/pre)$^A$ | PT prolongation (post/pre)$^A$ | ACT prolongation (post/pre)$^A$ | Cuticle bleedin time prolongation (post/pre)$^A$ |
|---|---|---|---|---|---|
| Control$^B$ | 18 | 1.10 ± 0.03 | 1.09 ± 0.01 | 0.97 ± 0.02 | 1.00 ± 0.03 |
| 10C12 - 3 μg/kg | 7 | 1.15 ± 0.05 | 1.08 ± 0.01 | 1.06 ± 0.02 | 0.90 ± 0.02 |
| - 6 μg/kg | 7 | 1.07 ± 0.03 | 1.08 ± 0.02 | 0.97 ± 0.03 | 0.92 ± 0.06 |
| - 10 μg/kg | 6 | 1.11 ± 0.06 | 1.06 ± 0.03 | 1.04 ± 0.03 | 1.01 ± 0.09 |

TABLE I-continued

Effects of 10C12 antibody on coagulation parameters in guinea pig. Data are mean ± SEM

| Rx | Number of animals | APTT prolongation (post/pre)[A] | PT prolongation (post/pre)[A] | ACT prolongation (post/pre)[A] | Cuticle bleedin time prolongation (post/pre)[A] |
|---|---|---|---|---|---|
| - 60 μg/kg | 3 | 1.18 ± 0.10 | 1.10 ± 0.01 | 1.01 ± 0.09 | 0.78 ± 0.04 |
| - 1000 μg/kg | 3 | 1.31 ± 0.07 | 1.04 ± 0.02 | 1.23 ± 0.14 | 0.97 ± 0.05 |

[A]Measurements taken before (pre-treatment) and 60 minutes after (post-treatment) Rx administration.
[B]pooled data from saline control and control antibody (NTN) experiments The effect of 10C12 on normal hemostasis was assessed by measuring the cuticle bleeding time, which has previously been shown to be coagulation dependent in dogs and rabbits. The bleeding time was measured before 10C12 administration (pre-value) and at the end of the experiment (post-value; 60 min after bolus administration). Despite its potent antithrombotic effect 10C12 did not prolong the cuticle bleeding time. Even at 1000 μg/kg the cuticle bleeding time remained unchanged (Table I). The effect of the highest dose of 10C12 (1000 μg/kg) on cuticle bleeding at an earlier time point was accessed in a separate group of guinea pigs. In these experiments the cuticle bleeding time, incidence of rebleeding and total blood loss were measured at 1 minute rather than 60 minutes post treatment. As shown in Table II, there was a trend towards an increase in these parameters in the 10C12 treated group. However, in no case was the increase statistically significant. Furthermore, in most cases (8 out of 9 in controls and 4 out of 6 in 10C12 treated) bleeding ceased entirely after primary hemostasis was complete.

TABLE II

Comparative effects of 10C12 antibody on cuticle bleeding in guinea pig and rat. Data are mean ± SEM

| Species Rx | Number of Animals | Cuticle bleeding time[A] (min) | Rebleed[B] (number) | Total blood loss[C] (mg) |
|---|---|---|---|---|
| guinea pig | | | | |
| Control[D] | 9 | 3.1 ± 0.4 | 1 | 90 ± 21 |
| 10C12 - 1000 μg/kg | 6 | 4.5 ± 0.7 | 2 | 137 ± 37 |
| rat | | | | |
| Control[D] | 10 | 2.5 ± 0.4 | 10 | 494 ± 105 |
| 10C12 - 1000 μg/kg | 10 | 2.6 ± 0.5 | 10 | 593 ± 197 |

[A]Measurements taken 1 minute after Rx aidministration
[B]number of animals which have a cuticle bleeding episode after initial cesation of bleeding
[C]total amount of blood shed over 30 minutes (from cuticle transection)
[D]pooled data from saline control and control antibody (NTN) experiments

Example

Administration of anti-IX/IXa gla Domain Antibodies Reduces Clot Weight and Duration of Vessel Occlusion in an Arterial Thrombosis Model.
Methods $FeCl_3$-induced arterial thrombosis model in the rat. The model of Kurz et al. (1990), Thromb. Res. 60:269–280, was modified as follows. Dosing and sampling catheters (PE 50 polyethylene tubing, Becton Dickinson and Co., Sparks, ML) were placed in the femoral vein and artery of an isoflorane anesthetized, Sprague Dawley, male rat (Harlan Labs, Indianapolis, Ind.). Rat body weights ranged from 420 to 460 grams. Body temperature was maintained at 37° C. throughout the surgical and experimental periods. The carotid artery was dissected free of its surrounding tissue and a ultrasonic flow probe (Transonic IR, Transonic Systems Inc., Itheca, N.Y.) was placed on the artery proximal to the heart. Thrombosis was induced by placing a slit polyethylene tubing (PE 205) containing a 3 mm diameter filter paper disc saturated with 70% $FeCl_3$ around the exposed artery cranial to the probe. Blood flow was monitored prior to and for 60 minutes following placement of the disc. 10C12, NTN or heparin were diluted to the appropriate concentration in sterile saline for injection. Various doses of 10C12 or NTN were administered as a single bolus of 1 ml. Heparin was administered as a loading bolus (100U/kg) followed by a constant infusion (1U/kg/min) over 65 minutes (total volume of 2 ml). Controls for the heparin administration consisted of saline for injection administered over the same time period and at the same volume. All treatments were administered via the venous catheter 5 minutes prior to disc placement. At one minute (NTN and 10C12 treatments) or 30 minutes (saline and heparin treatments) post dosing tail bleeding times were measured as described below. At 60 minutes, the artery was excised and any thrombus present was removed, blotted with filter paper and weighed. Thrombosis endpoints recorded were the incidence and duration of occlusion, and thrombus weight. Blood samples were drawn from the arterial catheter at predose and at 1, 35 and 65 minutes after dosing. These samples were analyzed for PT, APTT and ACT as described.

Measurements of tail bleeding time and blood loss in the rat thrombosis model. Tail bleeding time was determined by a modification of the free hand tail transection method described by Dejana et al. (1982), Thromb. Haemostasis 48:108–111). During the experimental period the rat was maintained supine on an elevated platform such that its tail was perpendicular to the plane of the body. Tail temperature was kept at 37° C. by placing it through the inner lumen of a water jacketed condenser (Kontes Glass, Baxter Healthcare Corp., Deerfield, Ill.) attached to a thermostatically controlled water recirculator (American Medical Systems, Cincinnati, Ohio). With this configuration, approximately 10 mm of the tail tip was accessible for transection. Tail bleeding times were measured following transection of 5 mm of the tail tip with a veterinary nail clipper (Resco model 727 with #400 blade, Tecla Co Inc, Walled Lake Mich.). This procedure was performed at one minute (NTN and 10C12 treatments) or 30 minutes (saline and heparin treatments) post dosing. These sampling times were selected to coincide with the time at which blood concentrations of the test reagents and therefore hemostatic effects were presumed to be near maximal for the bolus and infusion regimens used to administer the respective test reagents. Blood drops were collected at 30 second intervals into a pre-weighed microfuge tube. Bleeding time was recorded as the time before bleeding was completely arrested or drops required >30 seconds to form. At this time a second tube was placed under the tail to collect any additional blood (secondary blood loss) that was shed for up to 30 minutes after the tail transection. After this 30 minute collection period, the wound was cauterized to prevent additional blood loss. The total amount of blood lost over 30 minutes was determined by summing the weight of blood collected in the two tubes.

Additional cuticle bleeding time and blood loss experiments in guinea pig and rat. Because there were differences in how guinea pig cuticle bleeding and rat tail bleeding responded to 10C12 treatment, additional bleeding measurements were performed in order to identify the source of the discrepancy. In these additional experiments, the same methodology was used to measure bleeding in both guinea pigs and rats. Briefly, the animals were anesthetized and dosing catheters placed as described in the respective thrombosis models. However, blood samples, blood pressure or thrombosis measurements were not taken. One minute following administration of control (saline or NTN) or 1000 µg/kg of 10C12 as an IV bolus, the cuticle was transected and bleeding time, rebleeding and total blood loss where measured as described above for the rat tail bleeding assay.

Results

Antithrombotic and hemostatic effects of 10C12 and heparin in rat. The effects of 10C12 and heparin in the rat $FeCl_3$-induced arterial thrombosis model were examined. The antithrombotic efficacy was assessed by measuring the incidence and duration of vessel occlusion during the 60 min period following application of $FeCl_3$. In addition, the weight of thrombus recovered at the termination of the experiment was measured. Representative carotid artery blood flow tracings of a saline control and a 10C12 treated rat are shown in FIG. 13. Following bolus administration of the control antibody (NTN at 2000 µg/kg) none of the thrombotic nor any of the hemostatic endpoints were significantly different from the saline control. Therefore, saline and NTN control data were pooled for subsequent comparison to 10C12 and heparin treatments. Occlusion occurred in 10 out of 10 control animals at an average time of 14.1±1.5 min. With the exception of one animal, in which arterial flow briefly recovered before reoccluding, occlusion was sustained for the remainder of the experiment. The clot weight of controls was 2.8±0.2 mg and the duration of vessel occlusion was 44.7±2.6 min (FIG. 14). Administration of 10C12 at 500 µg/kg had no effect on either parameter nor on incidence of occlusion (5 out of 5). At 1000 µg/kg the incidence of occlusion decreased to 2 out of 5 (P≦0.05 vs control), while the clot weight was reduced to 0.66±0.17 mg (23.6±6.1% of control) and the duration of vessel occlusion decreased to 9.6±8.9 min (21.5±19.9% of control) (FIG. 14). At the highest dose of 2000 µg/kg, 10C12 further reduced the incidence of occlusion to 0 out of 5 (P≦0.001 versus control), while average clot weight decreased to 0.26±0.08 mg (9.2±2.3% of control) (FIG. 14). The effects on APTT/PT/ACT were determined from measurements in blood samples taken prior to and at multiple time points after drug administration. Since these parameters remained stable during the 60 minutes post dosing period, the 30 minute post dose values were selected for comparison to the predose value. 10C12 produced modest, dose dependent prolongation of the APTT and ACT whereas the PT was not affected (Table III), demonstrating the specificity of 10C12 in vivo. In comparison, administration of heparin (100U/kg bolus and 1U/kg/min infusion rate) had dramatic effects on the APTT in addition to affecting the ACT and PT (Table III) without completely reducing the clot weight or restoring vessel patency (FIG. 14).

TABLE III

Effects of 10C12 antibody and heparin on coagulation parameters in rat plasma.
Data are mean ± SEM

| Rx | Number of animals | APTT prolongation (post/pre)[A] | PT prolongation (post/pre)[A] | ACT prolongation (post/pre)[A] |
|---|---|---|---|---|
| Control[B] | 10 | 1.00 ± 0.02 | 0.98 ± 0.01 | 0.90 ± 0.03 |
| 10C12 - 500 µg/kg | 5 | 1.13 ± 0.14 | 0.97 ± 0.01 | 1.06 ± 0.02 * |
| - 1000 µg/kg | 5 | 1.23 ± 0.10 | 0.99 ± 0.01 | 1.14 ± 0.05 ** |
| - 2000 µg/kg | 5 | 1.67 ± 0.15 ** | 0.97 ± 0.02 | 1.20 ± 0.09 ** |
| Heparin - lU/kg/min | 5 | 12.1 ± 0.37 ** | 1.24 ± 0.09 ** | 2.16 ± 0.13 ** |

[A]Measurements taken before and 35 minutes after Rx administration.
[B]pooled data from saline control and control antibody (NTN) experiments
* P = 0.05,
** P = 0.01 (Mann-Whitney post hoc after Kruskal-Wallis Test)

As shown in table IV, none of the antithrombotically active doses of 10C12 prolonged the tail bleeding time. However, major effects of 10C12 on total blood loss were observed. In control animals, primary hemostasis at the transected tail was complete after 2.0±0.3 min and the weight of blood collected during this time period was 31.1±9.4 mg. In contrast to the transected guinea pig cuticle, all of the control tail wounds either continued to ooze blood (at a rate of less than one drop of blood per 0.5 minutes), or in some cases began to rebleed intermittently. In spite of oozing and/or resumed bleeding, the average blood loss during this secondary period was small (57.1±32.0 mg) relative to the time period (mean=48 minutes) over which the blood was collected. Administration of 10C12 exacerbated this secondary blood loss, thus increasing the total blood loss (Table IV). Although animal to animal variation was considerable, secondary blood loss increased in a dose dependent manner and the increase was statistically significant at all of the doses tested. Primary blood loss was not significantly affected. Heparin also caused increased cumulative blood loss. However, in contrast to 10C12 this increased bleeding was primarily due to delayed hemostatic plug formation reflected in prolonged tail bleeding times and increased primary blood loss (Table IV).

TABLE IV

Effects of 10C12 antibody and heparin on bleeding time and blood loss in the rat. Data are mean ± SEM

| Rx | Number of animals | Tail bleeding time[A] (min) | Primary blood[B] loss (mg) | Seconday blood[C] loss (mg) | Total blood loss[D] (mg) |
|---|---|---|---|---|---|
| Control[E] | 10 | 2.0 ± 0.3 | 31.1 ± 9.4 | 57.1 ± 32.0 | 88.2 ± 32.5 |
| 10C12 - 500 μg/kg | 5 | 2.0 ± 0.4 | 78.8 ± 41 | 424 ± 216 * | 503 ± 257 |
| - 1000 μg/kg | 5 | 2.3 ± 0.2 | 70.8 ± 25 | 473 ± 198 ** | 544 ± 209 ** |
| - 2000 μg/kg | 5 | 2.6 ± 0.8 | 117 ± 67 | 558 ± 280 ** | 674 ± 343 ** |
| Heparin - 1U/kg/min | 5 | 16.5 ± 5.6 ** | 319 ± 195 | 178 ± 77.2 | 497 ± 142 ** |

[A] Measurements taken 1 minute after Rx administration
[B] amount of blood shed during bleeding time measurement
[C] amount of blood shed after cessation of initial bleeding to 30 minutes after tail transection
[D] total amount of blood shed over 30 minutes (from tail transection)
[E] pooled data from saline control and control antibody (NTN) experiments
* $p = 0.05$,
** $p = 0.01$ (Mann-Whitney post hoc after Kruskal-Wallis Test)

Rat cuticle bleeding. Because the pattern of blood loss following 10C12 administration in the guinea pig cuticle and the rat tail were so different, cuticle bleeding experiments were performed in a separate group of rats. As in the rat tail bleeding experiments, oozing and or rebleeding occurred at the transected cuticle of both control and treated animals (10C12 at a dose of 100 μg/kg). However, in contrast to the tail bleeding assay, 10C12 did not enhance secondary bleeding at the rat cuticle, as there was no difference in cuticle bleeding time, incidence of rebleeding or total blood loss between control and 10C12 treated animals (Table II).

What is claimed is:

1. An isolated nucleic acid molecule comprising a nucleotide sequence encoding an antibody or antibody fragment thereof, wherein said antibody or antibody fragment:
   (a) specifically binds a factor IX/IXa Gla domain; and
   (b) comprises a heavy chain and a light chain variable region further wherein:
      (i) the heavy chain variable region comprises a CDR1 which is SEQ ID NO: 10, a CDR2 which is SEQ ID NO: 11 and a CDR3 which is SEQ ID NO: 12; and
      (ii) the light chain variable region comprises an 1cCDR1 which is SEQ ID NO: 13, an 1cCDR2 which is SEQ ID NO: 14, and an 1cCDR3 which is SEQ ID NO: 15.

2. A vector comprising the nucleic acid molecule of claim 1.

3. The vector of claim 2 operably linked to control sequences recognized by a host cell transformed with the vector.

4. A host cell comprising the vector of claim 2.

5. The host cell of claim 4, wherein said cell is a CHO cell.

6. The host cell of claim 4, wherein said cell is an *E. coli*.

7. The host cell of claim 4, wherein said cell is a yeast cell.

8. A method of producing an antibody or antibody fragment comprising culturing the host cell of claim 7 under condition wherein the isolated nucleic acid molecule is expressed.

* * * * *

UNITED STATES PATENT AND TRADEMARK OFFICE
CERTIFICATE OF CORRECTION

PATENT NO. : 6,624,295 B1  Page 1 of 1
DATED : September 23, 2003
INVENTOR(S) : Adams et al.

It is certified that error appears in the above-identified patent and that said Letters Patent is hereby corrected as shown below:

Column 6,
Line 10, after "fibrin", please replace "crosslienking" with -- crosslinking --.

Column 19,
Line 29, after "acid" and before "deg-", please replace "phosphatase.," with -- phosphatase, --.

Column 21,
Line 61, after "*Autographa*" and before "NPV", please replace "*califdrnica*" with -- *californica* --.

Column 24,
Line 47, before "variants", please replace "Antibady" with -- Antibody --.
Line 56, before "can be employed", please replace " collumn" with -- column --.

Signed and Sealed this

Eighteenth Day of November, 2003

JAMES E. ROGAN
*Director of the United States Patent and Trademark Office*